(12) United States Patent
DuBois et al.

(10) Patent No.: US 7,786,104 B2
(45) Date of Patent: Aug. 31, 2010

(54) N-(AMINOHETEROARYL)-1H-INDOLE-2-CARBOXAMIDE DERIVATIVES, AND PREPARATION AND THERAPEUTIC APPLICATION THEREOF

(75) Inventors: Laurent DuBois, Paris (FR); Yannick Evanno, Paris (FR); Andre Malanda, Paris (FR); David Machnik, Paris (FR); Catherine Gille, Paris (FR)

(73) Assignee: Sanofi-Aventis, Paris (FR)

( * ) Notice: Subject to any disclaimer, the term of this patent is extended or adjusted under 35 U.S.C. 154(b) by 21 days.

(21) Appl. No.: 12/359,468

(22) Filed: Jan. 26, 2009

(65) Prior Publication Data
US 2009/0156573 A1 Jun. 18, 2009

Related U.S. Application Data

(63) Continuation of application No. PCT/FR2007/001316, filed on Jul. 30, 2007.

(30) Foreign Application Priority Data

Jul. 31, 2006 (FR) .................................. 06 06988

(51) Int. Cl.
*A61K 31/00* (2006.01)
*A61K 31/44* (2006.01)
*A61K 31/404* (2006.01)
*C07D 401/14* (2006.01)
*C07D 205/04* (2006.01)

(52) U.S. Cl. .................... 514/210.2; 514/339; 514/415; 546/278.1; 548/466; 548/950

(58) Field of Classification Search ............. 546/278.1; 548/466, 950; 514/210.2, 339, 415
See application file for complete search history.

(56) References Cited

U.S. PATENT DOCUMENTS

| 4,104,385 | A | 8/1978 | Lesher et al. | |
| 7,223,788 | B2 * | 5/2007 | Schwink et al. | 514/426 |

FOREIGN PATENT DOCUMENTS

| GB | 870027 | 6/1961 |
| WO | WO 02/48152 | 6/2002 |
| WO | WO 2004/052869 | 6/2004 |
| WO | WO 2004/062665 | 7/2004 |
| WO | WO 2004/110985 | 12/2004 |
| WO | WO 2005/028445 | 3/2005 |
| WO | WO 2005/028452 | 3/2005 |
| WO | WO 2005/035526 | 4/2005 |
| WO | WO 2006/040522 | 4/2006 |
| WO | WO 2006/072736 | 7/2006 |
| WO | WO 2007/011284 | 1/2007 |
| WO | WO 2007/060140 | 5/2007 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Brands, M., et. al., Novel, Selective Indole-Based ECE Inhibitors: Lead Optimization Via Solid-Phase and Classical Synthesis, Bioorganic & Medicinal Chemistry Letters, vol. 15, (2005), pp. 4201-4205.
Derek, T., et. al., The Synthesis of Some 2-(Substituted) 5-Nitropyrimidines, Heterocycles, vol. 6, No. 12, (1977), pp. 1999-2004.
Fox, G. J., et. al., Bromination of 3-Amino- and 3-Dimethylamino-Pyridine, J. Chem. Soc. Perkin Trans 1, (1973), vol. 1, pp. 68-69.

* cited by examiner

Primary Examiner—Kamal A Saeed
Assistant Examiner—Samantha L Shterengarts
(74) Attorney, Agent, or Firm—Balaram Gupta

(57) ABSTRACT

The invention concerns compounds of general formula (I):

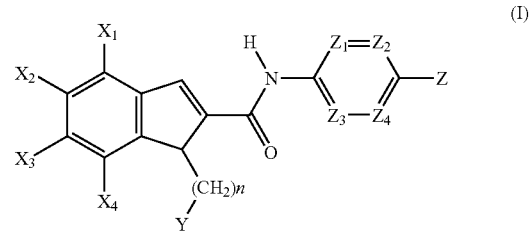

Wherein n, $X_1$, $X_2$, $X_3$, $X_4$, Y, Z, $Z_1$, $Z_2$, $Z_3$ and $Z_4$ are as defined herein. The invention also concerns a process for the preparation of compounds of formula (I) and their therapeutic use.

17 Claims, No Drawings

N-(AMINOHETEROARYL)-1H-INDOLE-2-CARBOXAMIDE DERIVATIVES, AND PREPARATION AND THERAPEUTIC APPLICATION THEREOF

This application is a continuation of International application No. PCT/FR2007/001,316, filed Jul. 30, 2007, which is incorporated herein by reference in its entirety; which claims the benefit of priority of French Patent Application No. 06/06, 988, filed Jul. 31, 2006.

The invention relates to N-(aminoheteroaryl)-1H-indole-2-carboxamide-derived compounds which exhibit in vitro and in vivo antagonist activity with respect to receptors of TRPV1 (or VR1) type.

A first subject of the invention relates to the compounds corresponding to formula (I) below.

Another subject of the invention relates to processes for preparing the compounds of formula (I).

Another subject of the invention relates to the use of the compounds of formula (I), in particular in medicaments or in pharmaceutical compositions.

The compounds of the invention correspond to formula (I):

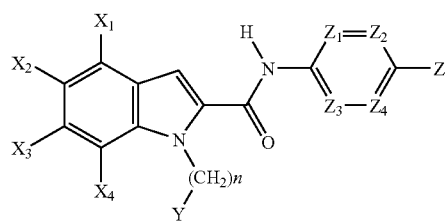

in which $X_1$ is a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, cyano, $C(O)NR_1R_2$, nitro, $C_1$-$C_6$-thioalkyl, —S(O)—$C_1$-$C_6$-alkyl, —S(O)$_2$—$C_1$-$C_6$-alkyl, $SO_2NR_1R_2$, aryl-$C_1$-$C_6$-alkylene, aryl or heteroaryl group, the aryl and heteroaryl being optionally substituted with one or more substituents selected from a halogen, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$X_2$ is a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, cyano, $C(O)NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, aryl-$C_1$-$C_6$-alkylene, aryl or heteroaryl group, the aryl and the heteroaryl being optionally substituted with one or more substituents selected from a halogen, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$X_3$ and $X_4$ are, independently of one another, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, cyano, $C(O)NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$, $NR_3SO_2R_5$, aryl-$C_1$-$C_6$-alkylene, aryl or heteroaryl group, the aryl and the heteroaryl being optionally substituted with one or more substituents selected from a halogen, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$Z_1$, $Z_2$, $Z_3$ and $Z_4$ are, independently of one another, a nitrogen atom or a $C(R_6)$ group, at least one corresponding to a nitrogen atom and at least one corresponding to a $C(R_6)$ group; the nitrogen atom or one of the nitrogen atoms present in the ring, defined as nitrogen in the 1-position, being optionally substituted with $R_7$ when the carbon atom in the 2- or 4-position with respect to this reference nitrogen is substituted with an oxo or thio group;

n is equal to 0, 1, 2 or 3;

Y is an aryl or a heteroaryl optionally substituted with one or more groups selected from a halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxy, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, cyano, $C(O)NR_1R_2$, nitro, $NR_1R_2$, $C_1$-$C_6$-thioalkyl, thiol, —S(O)—$C_1$-$C_6$-alkyl, —S(O)$_2$—$C_1$-$C_6$-alkyl, $SO_2NR_1R_2$, $NR_3COR_4$, $NR_3SO_2R_5$, aryl-$C_1$-$C_6$-alkylene or aryl group, the aryl and the aryl-$C_1$-$C_6$-alkylene being optionally substituted with one or more substituents selected from a halogen, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

Z is a cyclic amine attached via the nitrogen atom, of formula:

in which

A is a $C_1$-$C_7$-alkylene group optionally substituted with one or two groups $R_8$;

B is a $C_1$-$C_7$-alkylene group optionally substituted with one or two groups $R_9$;

L is a bond, or a sulfur, oxygen or nitrogen atom; the nitrogen atom being substituted with a group $R_{10}$ or $R_{11}$, the carbon atoms of the cyclic amine Z being optionally substituted with one or more groups $R_{12}$ which may be identical to or different from one another;

$R_1$ and $R_2$ are, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group; or $R_1$ and $R_2$ form, together with the nitrogen atom which bears them, an azetidinyl, pyrrolidinyl, piperidinyl, azepinyl, morpholinyl, thiomorpholinyl, piperazinyl or homopiperazinyl group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

$R_3$ and $R_4$ are, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

$R_5$ is a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

$R_6$ is a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, $C_1$-$C_6$-thioalkyl, —S(O)—$C_1$-$C_6$-alkyl, —S(O)$_2$—$C_1$-$C_6$-alkyl, aryl, aryl-$C_1$-$C_6$-alkylene, heteroaryl, hydroxy, thiol, oxo or thio group;

$R_7$ is a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, aryl, aryl-$C_1$-$C_6$-alkylene or heteroaryl group;

$R_8$, $R_9$ and $R_{10}$ are defined such that:

two groups $R_8$ can together form a bond or a $C_1$-$C_6$-alkylene group;

two groups $R_9$ can together form a bond or a $C_1$-$C_6$-alkylene group;

$R_8$ and $R_9$ can together form a bond or a $C_1$-$C_6$-alkylene group;

$R_8$ and $R_{10}$ can together form a bond or a $C_1$-$C_6$-alkylene group;

$R_9$ and $R_{10}$ can together form a bond or a $C_1$-$C_6$-alkylene group;

$R_{11}$ is a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, hydroxy, $COOR_5$, $C(O)NR_1R_2$, aryl-$C_1$-$C_6$-alkylene, aryl or heteroaryl group, the aryl and the heteroaryl being optionally substituted with one or more substituents selected from a halogen, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_1$-$C_6$-fluoroalkoxy, nitro or cyano group;

$R_{12}$ is a fluorine atom, a $C_1$-$C_6$-alkyl group optionally substituted with a group $R_{13}$, a $C_3$-$C_7$-cycloalkyl, $C_3$-$C_7$-cycloalkyl-$C_1$-$C_3$-alkylene, $C_1$-$C_6$-fluoroalkyl or $C_1$-$C_6$-cycloalkyl-1,1-idinyl group, a $C_3$-$C_7$-heterocycloalkyl-1,1-idinyl group optionally substituted on a nitrogen atom with a group $R_{11}$, or a $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, $C(O)NR_1R_2$, $NR_1R_2$, $NR_3COR_4$, $OC(O)NR_1R_2$, $NR_3COOR_5$, $NR_3CONR_1R_2$, hydroxy, thiol, oxo, thio, aryl-$C_1$-$C_6$-alkylene or aryl group, the aryl being optionally substituted with one or more substituents selected from a halogen, and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_1$-$C_6$-fluoroalkoxy, nitro or cyano group;

$R_{13}$ is a $C_1$-$C_6$-alkoxy, $C_3$-$C_7$-cycloalkoxy, $C_3$-$C_7$-cycloalkyl-$C_1$-$C_6$-alkylene-O—, $C(O)NR_1R_2$, $NR_1R_2$, $NR_3COR_4$, $OC(O)NR_1R_2$, $NR_3COOR_5$ or hydroxy.

In the compounds of formula (I), the nitrogen atom(s) can be in oxidized form (N-oxide). In the compounds of formula (I), the sulfur atom(s) can be in oxidized form (S(O) or $S(O)_2$).

By way of non-limiting examples of amines Z, mention may be made of aziridine, azetidine, pyrrolidine, piperidine, azepine, morpholine, thiomorpholine, piperazine, homopiperazine, azabicyclo[3.3.0]octanes, octahydrofuropyrroles, octahydropyrrolopyrroles, octahydroindole, octahydroisoindole, octahydropyrrolopyridines, decahydroquinoline, decahydroisoquinoline, decahydronaphthyridines, octahydropyridopyrazine, azabicylo[3.1.0]hexanes, azabicylo[3.2.0]heptanes, azabicylo[3.1.1]heptanes, diazabicylo[2.2.1]heptanes, azabicylo[3.2.1]octanes, diazabicylo[3.2.1]octanes and azabicylo[3.3.1]nonanes.

Among the compounds of formula (I) that are subjects of the invention, a first subgroup of compounds consists of the compounds for which $X_1$, $X_2$, $X_3$ and $X_4$ are selected, independently of one another, from a hydrogen or halogen atom or a $C_1$-$C_6$-alkyl, $C_1$-$C_6$-fluoroalkyl, $C_1$-$C_6$-thioalkyl or —S(O)$_2$—$C_1$-$C_6$-alkyl group.

Among the compounds of formula (I) that are subjects of the invention, a second subgroup of compounds consists of the compounds for which $X_1$, $X_2$, $X_3$ and $X_4$ are selected, independently of one another, from a hydrogen or halogen atom or a $C_1$-$C_6$-alkyl or $C_1$-$C_6$-fluoroalkyl group.

Among the compounds of formula (I) that are subjects of the invention, a third subgroup of compounds consists of the compounds for which $X_1$, $X_2$, $X_3$ and $X_4$ are selected, independently of one another, from a hydrogen, fluorine or chlorine atom or a methyl, ethyl, isopropyl, tert-butyl, trifluoromethyl, thiomethyl or —S(O)$_2$CH$_3$ group.

Among the compounds of formula (I) that are subjects of the invention, a fourth subgroup of compounds consists of the compounds for which $X_1$ is a hydrogen or halogen atom or a $C_1$-$C_6$-alkyl group;

$X_2$ is a hydrogen or halogen atom or a $C_1$-$C_6$-alkyl, $C_1$-$C_6$-fluoroalkyl or —S(O)$_2$—$C_1$-$C_6$-alkyl group;

$X_3$ and $X_4$ are, independently of one another, a hydrogen or halogen atom or a $C_1$-$C_6$-alkyl, $C_1$-$C_6$-fluoroalkyl, $C_1$-$C_6$-alkoxy, $NR_1R_2$ or $C_1$-$C_6$-thioalkyl group;

$R_1$ and $R_2$ are, independently of one another, a $C_1$-$C_6$-alkyl group.

Among the compounds of formula (I) that are subjects of the invention, a fifth subgroup of compounds consists of the compounds for which $X_1$ is a hydrogen, fluorine or chlorine atom or a methyl group;

$X_2$ is a hydrogen, fluorine or chlorine atom or a methyl, isopropyl, tert-butyl, trifluoromethyl or —S(O)$_2$CH$_3$ group;

$X_3$ and $X_4$ are, independently of one another, a hydrogen, fluorine or chlorine atom or a methyl, ethyl, isopropyl, tert-butyl, trifluoromethyl, —O-isopropyl, $NR_1R_2$ or thiomethyl group;

$R_1$ and $R_2$ are, independently of one another, a methyl group.

Among the compounds of formula (I) that are subjects of the invention, a sixth subgroup of compounds consists of the compounds for which $Z_1$, $Z_2$, $Z_3$ and $Z_4$ are, independently of one another, a nitrogen atom or a $C(R_6)$ group, at least two of them corresponding to a $C(R_6)$ group; the nitrogen atom or one of the nitrogen atoms present in the ring, defined as nitrogen in the 1-position, being optionally substituted with $R_7$ when the carbon atom in the 2- or 4-position with respect to this reference nitrogen is substituted with an oxo or thio group; $R_6$ and $R_7$ being as defined in formula (I).

Among the compounds of formula (I) that are subjects of the invention, a seventh subgroup of compounds consists of the compounds for which $Z_1$ and $Z_3$ are a $C(R_6)$ group and $Z_2$ and $Z_4$ are a nitrogen atom; $R_6$ being as defined in formula (I).

Among the compounds of formula (I) that are subjects of the invention, an eighth subgroup of compounds consists of the compounds for which $Z_1$ and $Z_3$ are a $C(R_6)$ group and $Z_2$ and $Z_4$ are a nitrogen atom; $R_6$ corresponding to a hydrogen atom.

Among the compounds of formula (I) that are subjects of the invention, a ninth subgroup of compounds consists of the compounds for which $Z_1$, $Z_2$, $Z_3$ and $Z_4$ are, independently of one another, a nitrogen atom or a $C(R_6)$ group, one corresponding to a nitrogen atom and the others corresponding to a $C(R_6)$ group; the nitrogen atom present in the ring, defined as nitrogen in the 1-position, being optionally substituted with $R_7$ when the carbon atom in the 2- or 4-position with respect to this reference nitrogen is substituted with an oxo or thio group; $R_6$ and $R_7$ being as defined in formula (I).

Among the compounds of formula (I) that are subjects of the invention, a tenth subgroup of compounds consists of the compounds for which $Z_4$ is a nitrogen atom and $Z_1$, $Z_2$ and $Z_3$ are, independently of one another, a $C(R_6)$ group; the nitrogen atom present in the ring, defined as nitrogen in the 1-position, being optionally substituted with $R_7$ when the carbon atom in the 2- or 4-position with respect to this reference nitrogen is substituted with an oxo or thio group; $R_6$ and $R_7$ being as defined in formula (I).

Among the compounds of formula (I) that are subjects of the invention, an eleventh subgroup of compounds consists of the compounds for which $Z_4$ is a nitrogen atom and $Z_1$, $Z_2$ and $Z_3$ are, independently of one another, a $C(R_6)$ group; $R_6$ is a hydrogen atom or a $C_1$-$C_6$-alkyl, $C_1$-$C_6$-fluoroalkyl or $C_1$-$C_6$-alkoxy group.

Among the compounds of formula (I) that are subjects of the invention, a twelfth subgroup of compounds consists of the compounds for which $Z_4$ is a nitrogen atom and $Z_1$, $Z_2$ and $Z_3$ are, independently of one another, a $C(R_6)$ group; $R_6$ is a hydrogen atom or a methyl, trifluoromethyl or methoxy group.

Among the compounds of formula (I) that are subjects of the invention, a thirteenth subgroup of compounds consists of the compounds for which n is equal to 1.

Among the compounds of formula (I) that are subjects of the invention, a fourteenth subgroup of compounds consists of the compounds for which Y is an aryl or a heteroaryl optionally substituted with one or more groups selected from a halogen atom or a $C_1$-$C_6$-alkyl or $NR_1R_2$ group;

$R_1$ and $R_2$ form, together with the nitrogen atom which bears them, an azetidinyl, pyrrolidinyl, piperidinyl, azepinyl, morpholinyl, thiomorpholinyl, piperazinyl or homopiperazinyl group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group.

Among the compounds of formula (I) that are subjects of the invention, a fifteenth subgroup of compounds consists of the compounds for which Y is a phenyl or a pyridinyl, the phenyl being optionally substituted with a group selected from a fluorine atom or a methyl or $NR_1R_2$ group;

$R_1$ and $R_2$ form, together with the nitrogen atom which bears them, a pyrrolidinyl group.

Among the compounds of formula (I) that are subjects of the invention, a sixteenth subgroup of compounds consists of the compounds for which Z is a cyclic amine attached via the nitrogen atom, of formula:

in which
A is a $C_1$-$C_4$-alkylene group optionally substituted with one or two groups $R_8$;
B is a $C_1$-$C_4$-alkylene group optionally substituted with one or two groups $R_9$;
L is a bond or an oxygen atom;

it being possible for the nitrogen atom of the cyclic amine Z to be in N-oxide form;

the carbon atoms of the cyclic amine Z being optionally substituted with a group $R_{12}$;

$R_8$ and $R_9$ are defined such that:
two groups $R_8$ can together form a bond; or
two groups $R_9$ can together form a bond; or
$R_8$ and $R_9$ can together form a bond;

$R_{12}$ is an $NR_1R_2$, $NR_3COOR_5$ or hydroxy group;

$R_1$ and $R_2$ are, independently of one another, a hydrogen atom;

$R_3$ is a hydrogen atom;

$R_5$ is a $C_1$-$C_6$-alkyl group.

Among the compounds of formula (I) that are subjects of the invention, a seventeenth subgroup of compounds consists of the compounds for which Z is a cyclic amine selected from azetidine, pyrrolidine, piperidine, morpholine, azabicylo[3.1.0]hexane and azabicylo[3.2.0]heptane;

it being possible for the nitrogen atom of the cyclic amine Z to be in N-oxide form;

the carbon atoms of the cyclic amine Z being optionally substituted with a group $R_{12}$;

$R_{12}$ is an $NR_1R_2$, $NR_3COOR_5$ or hydroxyl group;

$R_1$ and $R_2$, independently of one another, are a hydrogen atom;

$R_3$ is a hydrogen atom;

$R_5$ is a $C_1$-$C_6$-alkyl group.

Among the compounds of formula (I) that are subjects of the invention, an eighteenth subgroup of compounds consists of the compounds for which Z is a cyclic amine selected from azetidine, pyrrolidine, piperidine, morpholine, azabicylo[3.1.0]hexane and azabicylo[3.2.0]heptane;

it being possible for the nitrogen atom of the cyclic amine Z to be in N-oxide form;

the carbon atoms of the cyclic amine Z being optionally substituted with a group $R_{12}$;

$R_{12}$ is an $NR_1R_2$, $NR_3COOR_5$ or hydroxyl group;

$R_1$ and $R_2$ are, independently of one another, a hydrogen atom;

$R_3$ is a hydrogen atom;

$R_5$ is a tert-butyl group.

Among the compounds of formula (I) that are subjects of the invention, a nineteenth subgroup of compounds consists of the compounds for which Z is a cyclic amine selected from azetidine, pyrrolidine, piperidine, morpholine, azabicylo[3.1.0]hexane and azabicylo[3.2.0]heptane;

the carbon atoms of the azetidine being optionally substituted with a hydroxyl group;

the carbon atoms of the pyrrolidine being optionally substituted with an $NR_1R_2$, $NR_3COOR_5$ or hydroxyl group; it being possible for the nitrogen atom of the pyrrolidine to be in N-oxide form;

$R_1$ and $R_2$ are, independently of one another, a hydrogen atom;

$R_3$ is a hydrogen atom;

$R_5$ is a $C_1$-$C_6$-alkyl group.

Among the compounds of formula (I) that are subjects of the invention, a twentieth subgroup of compounds consists of the compounds for which Z is a cyclic amine selected from azetidine, pyrrolidine, piperidine, morpholine, azabicylo[3.1.0]hexane and azabicylo[3.2.0]heptane;

the carbon atoms of the azetidine being optionally substituted with a hydroxyl group;

the carbon atoms of the pyrrolidine being optionally substituted with an $NR_1R_2$, $NR_3COOR_5$ or hydroxyl group; it being possible for the nitrogen atom of the pyrrolidine to be in N-oxide form;

$R_1$ and $R_2$ are, independently of one another, a hydrogen atom;

$R_3$ is a hydrogen atom;

$R_5$ is a tert-butyl group.

Among the compounds of formula (I) that are subjects of the invention, a twenty-first subgroup of compounds consists of the compounds for which Z is a cyclic amine attached via the nitrogen atom, of formula:

in which
- A is a $C_1$-$C_7$-alkylene group optionally substituted with one or two groups $R_8$;
- B is a $C_1$-$C_7$-alkylene group optionally substituted with one or two groups $R_9$;
- L is a bond, or a sulfur, oxygen or nitrogen atom; the nitrogen atom being optionally substituted with a group $R_{10}$ or $R_{11}$, the carbon atoms of the cyclic amine Z being optionally substituted with one or more groups $R_{12}$, which may be identical to or different from one another, $R_{12}$ being a $C_1$-$C_6$-alkyl group optionally substituted with a group $R_{13}$, $NR_1R_2$ or $NR_3COOR_5$;

$R_1$ and $R_2$ are, independently of one another, a hydrogen atom or a $C_1$-$C_6$-alkyl group;

$R_3$ is a hydrogen atom or a $C_1$-$C_6$-alkyl group;

$R_5$ is a $C_1$-$C_6$-alkyl group;

$R_8$, $R_9$ and $R_{10}$ are defined such that:
- two groups $R_8$ can together form a bond or a $C_1$-$C_6$-alkylene group; or
- two groups $R_9$ can together form a bond or a $C_1$-$C_6$-alkylene group; or
- $R_8$ and $R_9$ can together form a bond or a $C_1$-$C_6$-alkylene group; or
- $R_8$ and $R_{10}$ can together form a bond or a $C_1$-$C_6$-alkylene group; or
- $R_9$ and $R_{10}$ can together form a bond or a $C_1$-$C_6$-alkylene group;

$R_{11}$ being as defined in the formula (I).

Among the compounds of formula (I) that are subjects of the invention, a twenty-second subgroup of compounds consists of the compounds for which Z is a cyclic amine attached via the nitrogen atom, of formula:

in which
- A is a $C_1$-$C_7$-alkylene group;
- B is a $C_1$-$C_7$-alkylene group;
- L is a bond, or a sulfur, oxygen or nitrogen group; the nitrogen atom being optionally substituted with a group $R_{11}$, the carbon atoms of the cyclic amine Z being optionally substituted with one or more groups $R_{12}$, which may be identical to or different from one another;

$R_{11}$ and $R_{12}$ being as defined in formula (I).

Among the compounds of formula (I) that are subjects of the invention, a twenty-third subgroup of compounds consists of the compounds for which Z is an azetidinyl, pyrrolidinyl, piperidinyl, azepinyl, morpholinyl, thiomorpholinyl, piperazinyl or homopiperazinyl group, this group being optionally substituted with one or more groups $R_{12}$, which may be identical to or different from one another; $R_{12}$ being as defined in formula (I).

Among the compounds of formula (I) that are subjects of the invention, a twenty-fourth subgroup of compounds consists of the compounds for which Z is a pyrrolidinyl, piperidinyl, morpholinyl or piperazinyl group, this group being optionally substituted with one or more groups $R_{12}$, which may be identical to or different from one another; $R_{12}$ being a $C_1$-$C_6$-alkyl group optionally substituted with a group $R_{13}$, $NR_1R_2$ or $NR_3COOR_5$;

$R_1$ and $R_2$ are, independently of one another, a hydrogen atom or a $C_1$-$C_6$-alkyl group;

$R_3$ is a hydrogen atom or a $C_1$-$C_6$-alkyl group;

$R_5$ is a $C_1$-$C_6$-alkyl group.

Among the compounds of formula (I) that are subjects of the invention, a twenty-fifth subgroup of compounds consists of the compounds for which $X_1$, $X_2$, $X_3$, $X_4$, $Z_1$, $Z_2$, $Z_3$, $Z_4$, n, Y and Z are as defined in the subgroups above.

Among the compounds of formula (I) that are subjects of the invention, a twenty-sixth subgroup of compounds consists of the compounds for which $X_1$, $X_2$, $X_3$ and $X_4$ are selected, independently of one another, from a hydrogen or halogen atom or a $C_1$-$C_6$-alkyl or $C_1$-$C_6$-fluoroalkyl group; and/or $Z_1$, $Z_2$, $Z_3$ and $Z_4$ are, independently of one another, a nitrogen atom or a $C(R_6)$ group, one corresponding to a nitrogen atom and the others corresponding to a $C(R_6)$ group; the nitrogen atom present in the ring, defined as nitrogen in the 1-position, being optionally substituted with $R_7$ when the carbon atom in the 2- or 4-position with respect to this reference nitrogen is substituted with an oxo or thio group; $R_6$ and $R_7$ being as defined in formula (I); and/or n is equal to 1; and/or Z is a cyclic amine attached via the nitrogen atom, of formula:

in which
- A is a $C_1$-$C_7$-alkylene group;
- B is a $C_1$-$C_7$-alkylene group;
- L is a bond, or a sulfur, oxygen or nitrogen atom; the nitrogen atom being optionally substituted with a group $R_{11}$, the carbon atoms of the cyclic amine Z being optionally substituted with one or more groups $R_{12}$, which may be identical to or different from one another;

$R_{11}$ and $R_{12}$ being as defined in formula (I).

Among the compounds of formula (I) that are subjects of the invention, mention may be made of the following compounds:

1. N-{6-[((R)-3-tert-butoxycarbonylamino)pyrrolidin-1-yl]pyridin-3-yl}-5-fluoro-1-(3-fluorobenzyl)-1H-indole-2-carboxamide
2. N-[6-(pyrrolidin-1-yl)pyridin-3-yl]-5-fluoro-1-(3-fluorobenzyl)-1H-indole-2-carboxamide
3. N-{6-[(R)-3-aminopyrrolidin-1-yl]pyridin-3-yl}-5-fluoro-1-(3-fluorobenzyl)-1H-indole-2-carboxamide
4. N-[6-(azetidin-1-yl)pyridin-3-yl]-5-fluoro-1-(3-fluorobenzyl)-1H-indole-2-carboxamide
5. N-[6-(pyrrolidin-1-yl)pyridin-3-yl]-5-trifluoromethyl-1-(3-fluorobenzyl)-1H-indole-2-carboxamide
6. N-[4-methyl-6-(pyrrolidin-1-yl)pyridin-3-yl]-5-fluoro-1-(3-fluorobenzyl)-1H-indole-2-carboxamide
7. N-[6-(3-hydroxypyrrolidin-1-yl)pyridin-3-yl]-5-fluoro-1-(3-fluorobenzyl)-1H-indole-2-carboxamide
8. N-[5-methoxy-6-(pyrrolidin-1-yl)pyridin-3-yl]-5-fluoro-1-(3-fluorobenzyl)-1H-indole-2-carboxamide
9. N-[6-(pyrrolidin-1-yl)pyridin-3-yl]-1-[(pyridin-4-yl)methyl]-6-trifluoromethyl-1H-indole-2-carboxamide
10. N-[6-(pyrrolidin-1-yl)-4-methylpyridin-3-yl]-5-fluoro-1-[(pyridin-4-yl)methyl]-1H-indole-2-carboxamide
11. N-[5-methoxy-6-(pyrrolidin-1-yl)pyridin-3-yl]-5-fluoro-1-[(pyridin-4-yl)methyl]-1H-indole-2-carboxamide
12. N-[6-(pyrrolidin-1-yl)pyridin-3-yl]-5-fluoro-1-[3-(pyrrolidin-1-yl)benzyl]-1H-indole-2-carboxamide
13. N-[6-(piperidin-1-yl)pyridin-3-yl]-5-fluoro-1-(3-fluorobenzyl)-1H-indole-2-carboxamide
14. N-[6-(pyrrolidin-1-yl)pyridin-3-yl]-1-[(pyridin-4-yl)methyl]-5-trifluoromethyl-1H-indole-2-carboxamide
15. N-[6-(pyrrolidin-1-yl)pyridin-3-yl]-5-fluoro-1-[(6-methylpyridin-2-yl)methyl]-1H-indole-2-carboxamide
16. N-[4-methoxy-6-(pyrrolidin-1-yl)pyridin-3-yl]-5-fluoro-1-(3-fluorobenzyl)-1H-indole-2-carboxamide
17. N-[6-(morpholin-4-yl)pyridin-3-yl]-5-fluoro-1-(3-fluorobenzyl)-1H-indole-2-carboxamide hydrochloride (1:1)
18. N-[4-methoxy-6-(pyrrolidin-1-yl)pyridin-3-yl]-5-fluoro-1-[(pyridin-4-yl)methyl]-1H-indole-2-carboxamide
19. N-[6-(pyrrolidin-1-yl)pyridin-3-yl]-5-fluoro-1-[(2-methylpyridin-4-yl)methyl]-1H-indole-2-carboxamide
20. N-[6-(1-oxypyrrolidin-1-yl)pyridin-3-yl]-5-fluoro-1-(3-fluorobenzyl)-1H-indole-2-carboxamide
21. N-[2-(pyrrolidin-1-yl)pyrimidin-5-yl]-5-fluoro-1-(3-fluorobenzyl)-1H-indole-2-carboxamide
22. N-[6-(3-azabicyclo[3.2.0]hept-3-yl)pyridin-3-yl]-5-fluoro-1-(3-fluorobenzyl)-1H-indole-2-carboxamide
23. N-[6-(pyrrolidin-1-yl)pyridin-3-yl]-1-[(pyridin-4-yl)methyl]-5-fluoro-1H-indole-2-carboxamide
24. N-[6-(3-hydroxyazetidin-1-yl)pyridin-3-yl]-5-fluoro-1-(3-fluorobenzyl)-1H-indole-2-carboxamide
25. N-[6-(azetidin-1-yl)pyridin-3-yl]-5-trifluoromethyl-1-(3-fluorobenzyl)-1H-indole-2-carboxamide
26. N-[6-(azetidin-1-yl)pyridin-3-yl]-1-[(pyridin-4-yl)methyl]-5-fluoro-1H-indole-2-carboxamide
27. N-[2-methyl-6-(pyrrolidin-1-yl)pyridin-3-yl]-5-fluoro-1-(3-fluorobenzyl)-1H-indole-2-carboxamide
28. N-[6-(3-azabicyclo[3.1.0]hex-3-yl)pyridin-3-yl]-5-fluoro-1-(3-fluorobenzyl)-1H-indole-2-carboxamide
29. N-[6-(3-hydroxyazetidin-1-yl)pyridin-3-yl]-1-(3-fluorobenzyl)-5-trifluoromethyl-1H-indole-2-carboxamide
30. N-[6-(3-hydroxyazetidin-1-yl)pyridin-3-yl]-1-(3-fluorobenzyl)-6-trifluoromethyl-1H-indole-2-carboxamide
31. N-[6-(azetidin-1-yl)pyridin-3-yl]-5-fluoro-1-(benzyl)-1H-indole-2-carboxamide
32. N-[6-(azetidin-1-yl)pyridin-3-yl]-4,6-dimethyl-1-(3-fluorobenzyl)-1H-indole-2-carboxamide
33. N-[6-(azetidin-1-yl)pyridin-3-yl]-6-tert-butyl-1-(3-fluorobenzyl)-1H-indole-2-carboxamide
34. N-[6-(azetidin-1-yl)pyridin-3-yl]-6-isopropyloxy-1-(3-fluorobenzyl)-1H-indole-2-carboxamide
35. N-[6-(azetidin-1-yl)pyridin-3-yl]-5-methylsulphonyl-1-(3-fluorobenzyl)-1H-indole-2-carboxamide
36. N-[6-(azetidin-1-yl)pyridin-3-yl]-6-dimethylamino-1-(3-fluorobenzyl)-1H-indole-2-carboxamide
37. N-[6-(azetidin-1-yl)pyridin-3-yl]-6-methylthio-1-(3-fluorobenzyl)-1H-indole-2-carboxamide
38. N-[6-(azetidin-1-yl)pyridin-3-yl]-4-fluoro-1-(3-fluorobenzyl)-1H-indole-2-carboxamide
39. N-[6-(azetidin-1-yl)pyridin-3-yl]-7-fluoro-1-(3-fluorobenzyl)-1H-indole-2-carboxamide
40. N-[6-(azetidin-1-yl)pyridin-3-yl]-6-fluoro-1-(3-fluorobenzyl)-1H-indole-2-carboxamide
41. N-[6-(azetidin-1-yl)pyridin-3-yl]-4-chloro-1-(3-fluorobenzyl)-1H-indole-2-carboxamide
42. N-[6-(azetidin-1-yl)pyridin-3-yl]-6-chloro-1-(3-fluorobenzyl)-1H-indole-2-carboxamide
43. N-[6-(azetidin-1-yl)pyridin-3-yl]-5-chloro-1-(3-fluorobenzyl)-1H-indole-2-carboxamide
44. N-[6-(azetidin-1-yl)pyridin-3-yl]-1-(3-fluorobenzyl)-1H-indole-2-carboxamide
45. N-[6-(azetidin-1-yl)pyridin-3-yl]-4-methyl-1-(3-fluorobenzyl)-1H-indole-2-carboxamide
46. N-[6-(azetidin-1-yl)pyridin-3-yl]-6-methyl-1-(3-fluorobenzyl)-1H-indole-2-carboxamide
47. N-[6-(azetidin-1-yl)pyridin-3-yl]-5-methyl-1-(3-fluorobenzyl)-1H-indole-2-carboxamide
48. N-[6-(azetidin-1-yl)pyridin-3-yl]-5-isopropyl-1-(3-fluorobenzyl)-1H-indole-2-carboxamide
49. N-[6-(azetidin-1-yl)pyridin-3-yl]-5-tert-butyl-1-(3-fluorobenzyl)-1H-indole-2-carboxamide
50. N-[6-(azetidin-1-yl)pyridin-3-yl]-6-ethyl-1-(3-fluorobenzyl)-1H-indole-2-carboxamide
51. N-[6-(azetidin-1-yl)pyridin-3-yl]-6-isopropyl-1-(3-fluorobenzyl)-1H-indole-2-carboxamide
52. N-[6-(azetidin-1-yl)pyridin-3-yl]-6-trifluoromethyl-1-(3-fluorobenzyl)-1H-indole-2-carboxamide 53. N-[6-(pyrrolidin-1-yl)-4-(trifluoromethyl)pyridin-3-yl]-5-fluoro-1-(3-fluorobenzyl)-1H-indole-2-carboxamide In the context of the present invention, the expression:

"$C_t$-$C_z$ where t and z can take the values of 1 to 7" is intended to mean a carbon-based chain that can contain from t to z carbon atoms, for example "$C_1$-$C_3$" is intended to mean a carbon-based chain which can contain from 1 to 3 carbon atoms;

"an alkyl" is intended to mean: a linear or branched, saturated aliphatic group. By way of examples, mention may be made of methyl, ethyl, propyl, isopropyl, butyl, isobutyl, tert-butyl, pentyl, etc., groups;

"an alkylene" is intended to mean: a linear or branched, saturated divalent alkyl group, for example a $C_1$-$C_3$-alkylene group is a linear or branched, divalent carbon-based chain containing from 1 to 3 carbon atoms, for example a methylene, ethylene, 1-methylethylene or propylene;

"a cycloalkyl" is intended to mean: a cyclic carbon-based group. By way of examples, mention may be made of cyclopropyl, cyclobutyl, cyclopentyl, cyclohexyl, etc., groups;

"a heterocycloalkyl" is intended to mean: a cyclic group with 3 to 7 ring members containing 1 or 2 heteroatoms chosen from O, S or N;

"a cycloalkyl-1,1-idinyl" or "a heterocycloalkyl-1,1-idinyl" is intended to mean: a group of the type

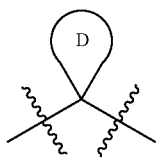

where D is a cycloalkyl or heterocycloalkyl group;

"a fluoroalkyl" is intended to mean: an alkyl group in which one or more hydrogen atoms have been substituted with a fluorine atom;

"an alkoxy" is intended to mean: an —O-alkyl radical where the alkyl group is as defined above;

"a cycloalkoxy" is intended to mean: an —O-cycloalkyl radical where the cycloalkyl group is as defined above;

"a fluoroalkoxy" is intended to mean: an alkoxy group in which one or more hydrogen atoms have been substituted with a fluorine atom;

"a thioalkyl" is intended to mean: an —S-alkyl radical where the alkyl group is as defined above;

"an aryl" is intended to mean: a cyclic aromatic group containing between 6 and 10 carbon atoms. By way of examples of aryl groups, mention may be made of phenyl or naphthyl groups;

"a heteroaryl" is intended to mean: an aromatic cyclic group with from 5 to 10 ring members containing from 1 to 4 heteroatoms chosen from O, S or N. By way of example, mention may be made of imidazolyl, thiazolyl, oxazolyl, furanyl, thiophenyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinolinyl, isoquinolinyl and quinoxalinyl groups;

"a halogen atom" is intended to mean: a fluorine, a chlorine, a bromine or an iodine;

"oxo" signifies "=O";

"thio" signifies "=S".

The compounds of formula (I) can contain one or more asymmetrical carbon atoms. They can therefore exist in the form of enantiomers or of diastereoisomers. These enantiomers and diastereoisomers, and also mixtures thereof, including racemic mixtures, are part of the invention.

The compounds of formula (I) can exist in the form of bases or of addition salts with acids. Such addition salts are part of the invention.

These salts are advantageously prepared with pharmaceutically acceptable acids, but the salts of other acids useful, for example, for the purification or the isolation of the compounds of formula (I) are also part of the invention.

The compounds of formula (I) can be in the form of hydrates or of solvates, i.e. in the form of associations or of combinations with one or more molecules of water or with a solvent. Such hydrates and solvates are also part of the invention.

In the text which follows, the term "leaving group" is intended to mean a group that can be readily cleaved from a molecule by cleavage of a heterolytic bond, with the departure of a pair of electrons. This group can thus be readily replaced with another group during a substitution reaction, for example. Such leaving groups are, for example, halogens or an activated hydroxyl group, such as a methanesulfonate, benzenesulfonate, p-toluenesulfonate, triflate, acetate, etc. Examples of leaving groups and also references for the preparation thereof are given in "Advances in Organic Chemistry", J. March, 5$^{th}$ Edition, Wiley Interscience, 2001.

In accordance with the invention, the compounds of formula (I) can be prepared according to the process illustrated by scheme 1 which follows.

According to scheme 1, the compounds of formula (IV) can be obtained by reaction of a compound of formula (II) in which $X_1$, $X_2$, $X_3$ and $X_4$ are as defined in formula (I) and B is a $C_1$-$C_6$-alkoxyl group, with a compound of formula (III), in which Y and n are as defined in formula (I) and GP is a leaving group where GP is a hydroxyl group.

The compounds of formula (II) are commercially available or prepared according to many processes described in the literature (D. Knittel *Synthesis* 1985, 2, 186; T. M. Williams *J. Med. Chem.* 1993, 36 (9), 1291; JP2001151771A2, for example).

When the compound of formula (III) is defined such that n is equal to 1, 2 or 3 and GP is a leaving group such as a chlorine, bromine or iodine atom, the reaction can be carried out in the presence of a base such as sodium hydride or potassium carbonate, in a polar solvent such as dimethylformamide, dimethyl sulfoxide or acetone (n=1: Kolasa T., *Bioorg. Med. Chem.* 1997, 5 (3) 507, n=2: Abramovitch R., *Synth. Commun.*, 1995, 25 (1), 1).

When the compound of formula (III) is defined such that n is equal to 1, 2 or 3 and GP is a hydroxyl group, the compounds of formula (IV) can be obtained by reaction of the compound of formula (II) with a compound of formula (III) in the presence of a phosphine such as, for example, triphenylphosphine, and of a reactant such as, for example, diethyl azodicarboxylate in solution in a solvent such as dichloromethane or tetrahydrofuran (O. Mitsonobu, *Synthesis*, 1981, 1-28).

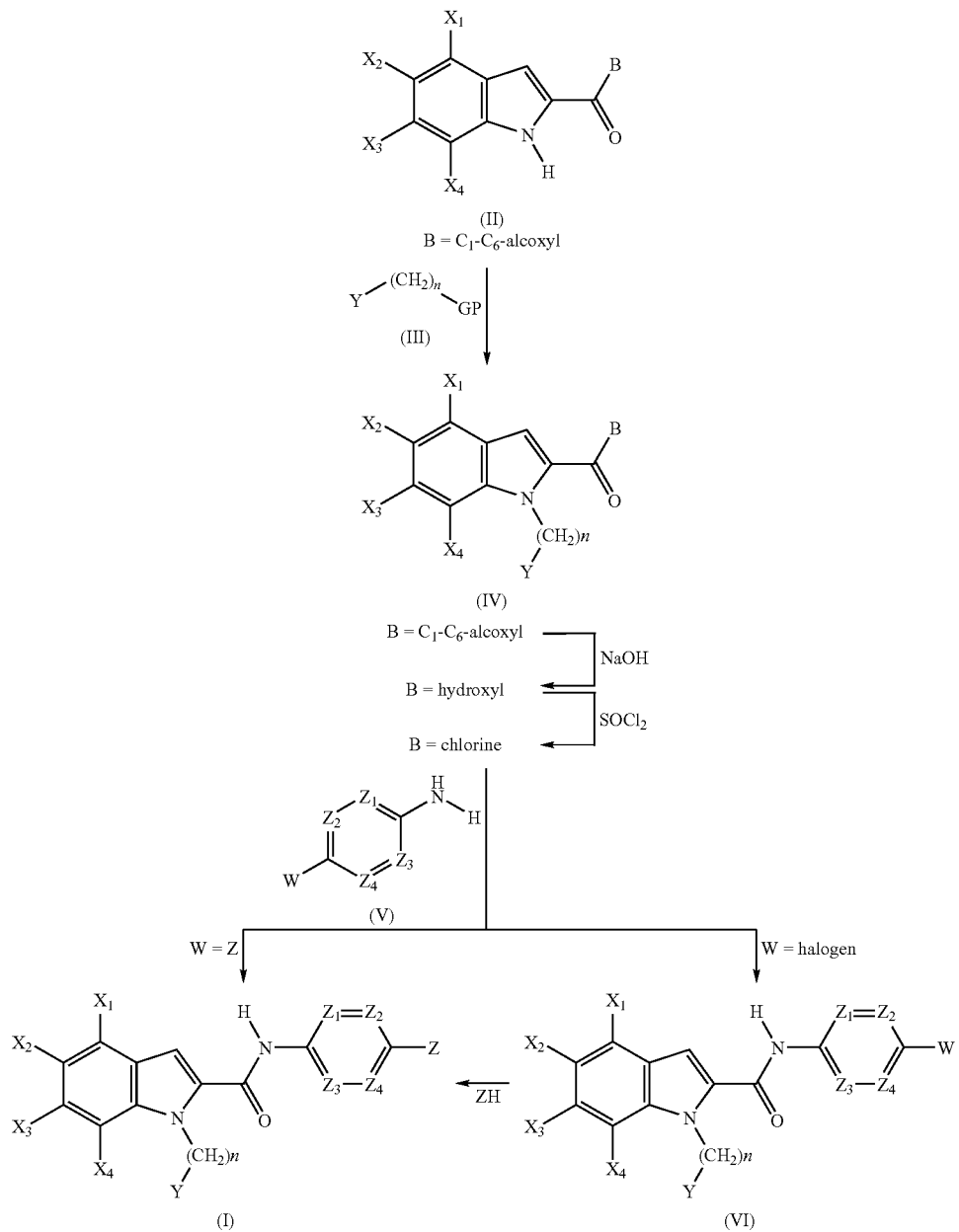

Scheme 1

When the compound of formula (III) is defined such that n is equal to 0, GP is a leaving group such as a chlorine, bromine or iodine atom and the reaction can be carried out at a temperature of between 80° C. and 250° C., in the presence of a copper-based catalyst such as copper bromide or copper oxide, and also of a base such as potassium carbonate (Murakami Y., *Chem. Pharm. Bull.*, 1995, 43 (8), 1281). The milder conditions described in S. L. Buchwald, *J. Am. Chem. Soc.* 2002, 124, 11 684 can also be used.

The compound of formula (IV), for which B is a $C_1$-$C_6$-alkoxyl group, can be converted to a compound of formula (IV) where B is a hydroxyl group, by the action of a base such as sodium hydroxide or potassium hydroxide in solution in a solvent such as ethanol. The compound of formula (IV) where B is a hydroxyl group can, subsequently, be converted to a compound of formula (IV) where B is a chlorine atom, by the action of a chlorinating agent such as thionyl chloride in a solvent such as dichloromethane.

The compounds of formulae (I) and (VI) can subsequently be obtained, for example, by reaction of a compound of formula (IV) where B is a chlorine atom, as obtained above, with an amine of formula (V), in which $Z_1$, $Z_2$, $Z_3$ and $Z_4$ are as defined in formula (I), and W is a halogen atom, such as a chlorine, a bromine or an iodine, or with a cyclic amine Z as defined in formula (I), in a solvent such as dichloroethane, toluene or tetrahydrofuran. The compounds of formulae (I) and (VI) can also be obtained by reaction of a compound of formula (IV) where B is a hydroxyl group, as obtained above, with an amine of formula (V), in which $Z_1$, $Z_2$, $Z_3$ and $Z_4$ are as defined in formula (I) and W is a halogen atom, such as a chlorine, a bromine or an iodine, or with a cyclic amine Z as defined in formula (I), in the presence of a coupling agent such as diethylcyanophosphonate, in the presence of a base such as triethylamine, in a solvent such as dimethylformamide, or in the presence of a coupling agent such as N-(3-dimethylaminopropyl)-N'-ethylcarbodiimide, in the presence of N-1-hydroxybenzotriazole, in a solvent such as dimethylformamide. When W is a halogen atom, a compound of (VI) is obtained. When W is a cyclic amine Z as defined in the formula of (I), a compound of formula (I) is obtained.

The compound of formula (I) can also be obtained by reaction of a compound of formula (VI) where W is a halogen atom, in the presence of an amine of formula ZH in which Z is a cyclic amine as defined in general formula (I), without solvent or in a solvent such as N-methylpyrrolidinone, or else by application of a catalyzed N-arylation method such as that described by J. Hartwig (J. F. Hartwig, *Angew Chem. Int. Ed.* 2005, 44, 1371-1375), preferably under an inert atmosphere, in the presence of a base such as lithium bistrimethylsilylamide in the presence of a source of palladium in catalytic amount, such as palladium diacetate, and of a catalytic amount of a palladium ligand, such as a phosphine, the whole in solution in a solvent such as dimethoxyethane (DME).

The compounds of formulae (I), (II) and (IV), in which $X_1$, $X_2$, $X_3$ and/or $X_4$ are a cyano group or an aryl, can be obtained by a coupling reaction, catalyzed by a metal such as palladium, carried out on the corresponding compounds of formulae (I), (II) and (IV) in which $X_1$, $X_2$, $X_3$ and/or $X_4$ are a leaving group, for example a bromine, according to methods which are described in the literature or which are known to those skilled in the art.

The compounds of formulae (I), (II) and (IV), in which $X_1$, $X_2$, $X_3$ and/or $X_4$ are a C(O)NR$_1$R$_2$ group, can be obtained from the corresponding compounds of formulae (I), (II) and (IV) in which $X_1$, $X_2$, $X_3$ and/or $X_4$ are a cyano group, according to methods which are described in the literature or which are known to those skilled in the art.

The compounds of formulae (I), (II) and (IV), in which $X_1$, $X_2$, $X_3$, $X_4$ and/or $R_6$ are an —S(O)-alkyl or —S(O)$_2$-alkyl group, can be obtained by oxidation of the corresponding compounds of formulae (I), (II) and (IV) in which $X_1$, $X_2$, $X_3$, $X_4$ and/or $R_6$ are a C$_1$-C$_6$-thioalkyl group, according to methods which are described in the literature or which are known to those skilled in the art.

Similarly, the compounds of formulae (I) and (IV), in which Y is substituted with an —S(O)-alkyl or —S(O)$_2$-alkyl group, can be obtained by oxidation of the corresponding compounds of formulae (I) and (IV) in which Y is substituted with a C$_1$-C$_6$-thioalkyl group, according to methods which are described in the literature or which are known to those skilled in the art.

The compounds of formula (I) in which $Z_1$, $Z_2$, $Z_3$ and/or $Z_4$ are a C—R$_6$ group corresponding to a C—OH group, can be obtained starting from the corresponding compounds of formula (I) in which $Z_1$, $Z_2$, $Z_3$ and/or $Z_4$ are a C—R$_6$ group corresponding to a C$_1$-C$_6$-alkoxyl group, according to methods which are described in the literature or which are known to those skilled in the art.

The compounds of formulae (I), (II) and (IV), in which $X_1$, $X_2$, $X_3$ and/or $X_4$ are an NR$_1$R$_2$, NR$_3$COR$_4$ or NR$_3$SO$_2$R$_5$ group, can be obtained from the corresponding compounds of formulae (I), (II) and (IV) in which $X_1$, $X_2$, $X_3$ and/or $X_4$ are a nitro group, for example by reduction, and then acylation or sulfonylation, according to methods which are described in the literature or which are known to those skilled in the art.

The compounds of formulae (I), (II) and (IV), in which $X_1$, $X_2$, $X_3$ and/or $X_4$ are an NR$_1$R$_2$, NR$_3$COR$_4$ or NR$_3$SO$_2$R$_5$ group, can be obtained from the corresponding compounds of formulae (I), (II) and (IV) in which $X_1$, $X_2$, $X_3$ and/or $X_4$ are, for example, a bromine atom, by coupling reaction respectively with an amine, an amide or a sulfonamide in the presence of a base, of a phosphine and of a palladium-based catalyst, according to methods which are described in the literature or which are known to those skilled in the art.

The compounds of formulae (I), (II) and (IV), in which $X_1$, $X_2$, $X_3$ and/or $X_4$ are an SO$_2$NR$_1$R$_2$ group, can be obtained by a method similar to that described in *Pharmazie* 1990, 45, 346, or according to methods which are described in the literature or which are known to those skilled in the art.

The compounds of formula (III) are commercially available, described in the literature (Carling R. W. et al *J. Med. Chem.* 2004 (47), 1807-1822 or Russel M. G. N. et al. *J. Med. Chem.* 2005 (48), 1367-1383) or accessible using methods known to those skilled in the art. Certain compounds of formula (IV) are described in the literature (WO 07/010,144, for example). The compounds (V) and the other reactants, when the method for preparing them is not described, are commercially available or described in the literature (WO 05/028452, WO 02/048152, WO 06/040522, WO 04/052869, *Heterocycles* 1977, 6(12), 1999-2004, *J. Chem. Soc. Perkin trans* 1, 1973 (1) 68-69, JP07/051,121, WO 05/035526, WO 07/011, 284, WO 04/062665, GB 870027, U.S. Pat. No. 4,104,385).

According to another of its aspects, a subject of the invention is also the compounds of formulae (Va), (Vb), (Vc), (Vd), (Ve), (Vf), (Vg). These compounds are useful as intermediates for the synthesis of the compounds of formula (I).

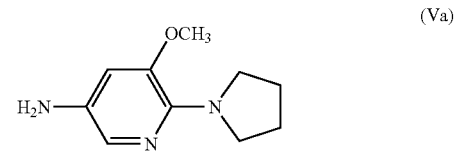

(Va)

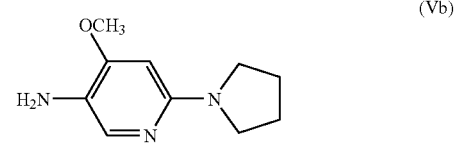

(Vb)

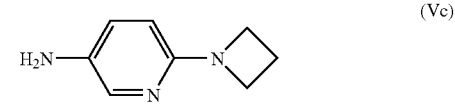

(Vc)

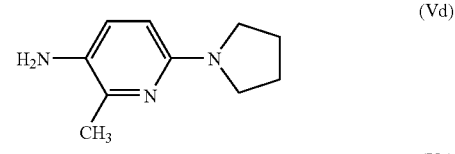

(Vd)

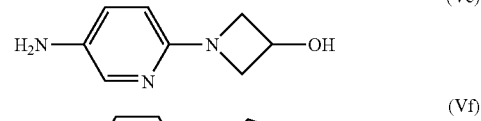

(Ve)

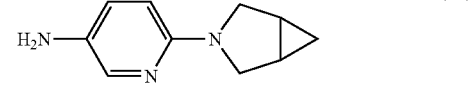

(Vf)

-continued

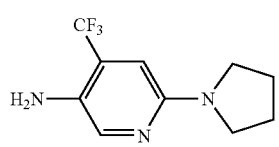

(Vg)

The amines of formulae (Va), (Vb), (Vc), (Vd), (Ve), (Vf), (Vg) can be prepared, for example, according to the process described in example no. 5, by aromatic nucleophilic substitution of a 6-chloropyridine precursor which is optionally substituted (Va: with a 5-methoxy group, Vb: with a 4-methoxy group, Vd: with a 2-methyl group, Vg: with a 4-trifluoromethyl group), with an amine, such as pyrrolidine, for example in a solvent such as ethanol. Access to the amines Va-g can subsequently require the reduction of a nitro group, for example, by catalytic hydrogenation in the presence of a catalyst such as palladium-on-charcoal, or by any other methods known to those skilled in the art, for the reduction of a nitro group to an amine. The amines of formulae (Va), (Vb), (Vc), (Vd), (Ve), (Vf), (Vg) were prepared in the form of a powder or of an oil, in the form of a base or of an addition salt with an acid. Table 1 gives the $^1$H NMR data for these amines.

TABLE 1

| No. | $^1$H NMR, δ (ppm): |
|---|---|
| Va | In CDCl$_3$, δ (ppm): 2.5 (m, 4H); 3.23 (broad peak, 2H); 3.49 (m, 4H); 3.91 (s, 3H); 5.90 (s, 1H); 7.71 (s, 1H). |
| Vb | In DMSO D$_6$, δ (ppm): 1.81 (m, 4H); 3.29 (m, 4H); 3.71 (s, 3H); 4.52 (broad peak, 2H); 6.61 (s, 1H); 7.16 (s, 1H). |
| Vc | In DMSO D$_6$, δ (ppm): 2.21 (m, 2H); 3.78 (m, 4H); 4.42 (broad peak, 2H); 6.20 (d, 1H); 6.89 (d, 1H); 7.58 (s, 1H). |
| Vd | In CDCl$_3$, δ (ppm): 1.89 (m, 4H); 2.23 (s, 3H); 2.98 (broad peak, 2H); 3.31 (m, 4H); 6.03 (d, 1H); 6.82 (d, 1H). |
| Ve | In DMSO D$_6$, δ (ppm): 3.49 (m, 2H); 3.98 (m, 2H); 4.48 (broad peak, 3H); 5.48 (broad peak, 1H); 6.22 (d, 1H); 6.91 (d, 1H); 7.58 (s, 1H). |
| Vf | In DMSO D$_6$, δ (ppm): 0.2 (m, 1H); 0.66 (m, 1H); 1.6 (m, 2H); 3.11 (m, 2H); 3.51 (d, 2H); 4.32 (broad peak, 2H); 6.25 (d, 1H); 6.99 (d, 1H); 7.55 (s, 1H). |
| Vg | In DMSO D$_6$, δ (ppm): 2 (m, 4H); 3.52 (m, 4H); 7.1 (s, 1H); 7.49 (broad peak, 2H); 7.92 (s, 1H); hydrochloride form 1:1 |

The following examples describe the preparation of certain compounds in accordance with the invention. These examples are not limiting and merely illustrate the present invention. The numbers of the compounds exemplified refer to those given in Table 2. The elemental microanalyses, the LC-MS (liquid chromatography coupled to mass spectrometry) analyses, the IR spectra or the NMR spectra confirm the structures of the compounds obtained.

EXAMPLE 1

Compound No. 1

N-{6-[((R)-3-tert-Butoxycarbonylamino)pyrrolidin-1-yl]pyridin-3-yl}-5-fluoro-1-(3-fluorobenzyl)-1H-indole-2-carboxamide 1.1.
5-Fluoro-1-(3-fluorobenzyl)-1H-indole-2-carboxylic Acid An aqueous solution of sodium hydroxide, prepared from 1.15 g (28.92 mmol) of sodium hydroxide pellets in 50 ml of water, is added to a solution of 7.6 g (24.10 mmol) of ethyl 5-fluoro-1-(3-fluorobenzyl)-1H-indole-2-carboxylate (WO 2006/024776) in 241 ml of ethanol. The mixture is heated for two hours and then concentrated under reduced pressure. The resulting solid is taken up in 200 ml of water. The solution is washed with twice 100 ml of ethyl ether, acidified by successive additions of small amounts of concentrated hydrochloric acid, and then extracted with 200 ml of ethyl acetate. The organic phase is finally washed twice with 100 ml of water and once with 50 ml of a saturated sodium chloride solution, dried over magnesium sulfate, and concentrated under reduced pressure. After drying at 50° C. under reduced pressure, 6.4 g of the expected product are obtained in the form of a solid, which will be used as it is in the next step.

1.2 N-{6-[((R)-3-tert-Butoxycarbonylamino)pyrrolidin-1-yl]pyridin-3-yl}-5-fluoro-1-(3-fluorobenzyl)-1H-indole-2-carboxamide (Compound no. 1)

0.85 ml (4.91 mmol) of diisopropylethylamine is added, dropwise, at 20° C. under argon, to a solution of 0.47 g (1.64 mmol) of 5-fluoro-1-(3-fluorobenzyl)-1H-indole-2-carboxylic acid (obtained in step 1.1), of 0.5 g (1.8 mmol) of 3-amino-6-[((R)-3-tert-butoxycarbonylamino)pyrrolidin-1-yl]pyridine (JP2004175739) and of 0.85 g (1.64 mmol) of trispyrrolidinophosphonium hexafluorophosphate (PYBOP) in 20 ml of dichloromethane. The mixture is stirred at ambient temperature for 12 hours, concentrated under reduced pressure, and then taken up with 50 ml of ethyl acetate. This solution is then successively washed with three times 15 ml of a saturated sodium hydrogen carbonate solution and 20 ml of a saturated sodium chloride solution and then dried over sodium sulfate, filtered and concentrated under reduced pressure. The product obtained is purified by silica column chromatography, elution being carried out with a mixture of dichloromethane and methanol. The resulting solid is then triturated in ethyl ether. 0.788 g of a solid is obtained, which solid is dried under reduced pressure.

Melting point: 207-209° C.
$^1$H NMR (DMSO D$_6$), δ (ppm): 1.49 (s, 9H); 1.85 (sext, 1H); 2.1 (sext, 1H); 3.2 (m, 4H); 4.09 (m, 1H); 5.88 (s, 2H); 6.41 (d, 1H); 7.04 (m, 7H); 7.61 (m, 2H); 7.8 (dxd, 1H); 8.31 (d, 1H); 10.19 (s, 1H).

EXAMPLE 2

Compound No. 2

N-[6-(Pyrrolidin-1-yl)pyridin-3-yl]-5-fluoro-1-(3-fluorobenzyl)-1H-indole-2-carboxamide 0.28 ml (1.68 mmol) of diethyl cyanophosphonate is added, dropwise, at 20° C. under argon, to a solution of 0.402 g (1.4 mmol) of 5-fluoro-1-(3-fluorobenzyl)-1H-indole-2-carboxylic acid (example 1.1) and of 0.274 g (1.68 mmol) of 3-amino-6-(pyrrolidin-1-yl)pyridine (WO 02/48152) in 10 ml of dry dimethylformamide. The mixture is stirred for ten minutes and then 0.43 ml (3.08 mmol) of triethylamine is added dropwise. The mixture is stirred at ambient temperature for 18 hours, concentrated under reduced pressure, and then taken up with 50 ml of ethyl acetate. This solution is then successfully washed with three times 20 ml of a saturated sodium hydrogen carbonate solution, 50 ml of water and 20 ml of a saturated sodium chloride solution, and then dried over sodium sulfate, filtered, and concentrated under reduced pressure. The solid obtained is triturated in isopropylether under hot conditions. 0.527 g of a solid is obtained, which solid is dried under reduced pressure.

Melting point: 199-201° C.

$^1$H NMR (DMSO $D_6$), δ (ppm): 1.9 (m, 4H); 3.3 (m, 4H); 5.82 (s, 2H); 6.4 (d, 1H); 7.04 (m, 6H); 7.51 (m, 2H); 7.77 (dxd, 1H); 8.3 (d, 1H); 10.25 (s, 1H)

EXAMPLE 3

Compound No. 4

N-[6-(Azetidin-1-yl)pyridin-3-yl]-5-fluoro-1-(3-fluorobenzyl)-1H-indole-2-carboxamide 3.1 N-[6-chloropyridin-3-yl]-5-fluoro-1-(3-fluorobenzyl)-1H-indole-2-carboxamide 23.8 ml (47.57 mmol) of a 2M solution of trimethylaluminum in toluene are added to a solution, stirred at 20° C. under an argon atmosphere, of 4.48 g (34.89 mmol) of 6-chloro-3-aminopyridine in 317 ml of toluene. The solution is then brought to 120° C. and 10 g (31.71 mmol) of ethyl 5-fluoro-1-(3-fluorobenzyl)-1H-indole-2-carboxylate are added in several steps (WO 2006/024776). The reaction mixture is refluxed for 4 hours and is then cooled to 0° C. 15 ml of water are added to the reaction medium, which is then extracted with twice 200 ml of ethyl acetate. The organic phases are combined and washed twice with 50 ml of water and once with 50 ml of a saturated sodium chloride solution, and then dried over magnesium sulfate and concentrated under reduced pressure. The residue obtained is triturated in 100 ml of ethyl ether, the product is filtered, and 10 g of expected product are recovered in the form of a powder.

$^1$H NMR (DMSO $D_6$), δ (ppm): 5.9 (s, 2H); 6.9 (m, 2H); 7.05 (txd, 1H); 7.2 (txd, 1H); 7.32 (m, 1H); 7.58 (m, 4H); 8.25 (d, 1H); 8.79 (s, 1H); 10.79 (s, 1H)

3.2 N-[6-(Azetidin-1-yl)pyridin-3-yl]-5-fluoro-1-(3-fluorobenzyl)-1H-indole-2-carboxamide (Compound no. 4)

4.2 ml (4.2 mmol) of a 1M solution of lithium bistrimethylsilylamide in tetrahydrofuran are added to a mixture, stirred to 0° C. under an argon atmosphere, of 0.7 g (1.76 mmol) of N-[6-chloropyridin-3-yl]-5-fluoro-1-(3-fluorobenzyl)-1H-indole-2-carboxamide, prepared in step 3.1, of 0.123 g (2.11 mmol) of azetidine, of 8 mg (0.04 mmol) of palladium diacetate and of 19.5 mg (0.04 mmol) of (R)-(−)-1-[(S)-2-(dicyclohexylphosphino)ferrocenyl]ethyldi-tert-butylphosphine in 1.8 ml of dry and degassed dimethoxyethane. The reactor is closed and then heated at 100° C. for 16 hours. The reaction mixture is then poured into 50 ml of water. 5 ml of a molar solution of hydrochloric acid and then 50 ml of a saturated sodium hydrogencarbonate solution are added slowly. The mixture is extracted twice with 50 ml of ethyl acetate. The organic phases are combined and then washed twice with 50 ml of a saturated sodium hydrogen carbonate solution, dried over magnesium sulfate and then concentrated under reduced pressure. The product obtained is purified by silica column chromatography, elution being carried out with a mixture of dichloromethane and acetone. The resulting solid is then triturated in 20 ml of hot isopropanol, recovered by filtration, and then recrystallized from a mixture of ethanol and methanol. 0.31 g of a solid is recovered by filtration, and dried under reduced pressure.

Melting point: 227-228° C.

$^1$H NMR (DMSO $D_6$), δ (ppm): 2.25 (pent, 2H); 3.9 (t, 4H); 6.01 (s, 2H); 6.35 (d, 1H); 6.89 (m, 2H); 7.01 (txd, 1H); 7.12 (txd, 1H); 7.19 (q, 1H); 7.34 (s, 1H); 7.52 (m, 2H); 7.82 (dxd, 1H); 8.31 (s, 1H); 10.28 (s, 1H).

EXAMPLE 4

Compound No. 7

N-[6-(3-Hydroxypyrrolidin-1-yl)pyridin-3-yl]-5-fluoro-1-(3-fluorobenzyl)-1H-indole-2-carboxamide A mixture of 0.4 g (1.01 mmol) of N-[6-chloropyridin-3-yl]-5-fluoro-1-(3-fluorobenzyl)-1H-indole-2-carboxamide, prepared in step 3.1, and 0.81 ml (10.06 mmol) of 3-hydroxypyrrolidine in 1.2 ml of N-methylpyrrolidinone is heated for 20 minutes in a microwave oven regulated at 200° C. under 300 watts. The reaction mixture is then poured into 50 ml of water. A solid is recovered by filtration and purified by silica column chromatography, elution being carried out with a mixture of dichloromethane and methanol. The resulting solid is then recrystallized from a mixture of methanol and dichloromethane. 0.22 g of a solid is recovered by filtration and dried under reduced pressure.

Melting point: 229-230° C.

$^1$H NMR (DMSO $D_6$), δ (ppm): 1.9 (m, 1H); 2.04 (m, 1H); 3.3-3.47 (m, 4H); 4.49 (s, 1H); 4.92 (s, 1H); 5.9 (s, 2H); 6.47 (d, 1H); 6.91 (m, 2H); 7.05 (txd, 1H); 7.12 (txd, 1H); 7.31 (q, 1H); 7.39 (s, 1H); 7.55 (m, 2H); 7.82 (dxd, 1H); 8.37 (s, 1H); 10.22 (s, 1H).

EXAMPLE 5

Compound No. 8

N-[5-Methoxy-6-(pyrrolidin-1-yl)pyridin-3-yl]-5-fluoro-1-(3-fluorobenzyl)-1H-indole-2-carboxamide 5.1 3-Methoxy-5-nitro-2-(pyrrolidin-1-yl)pyridine A solution of 3 g (15.91 mmol) of 2-chloro-3-methoxy-5-nitropyridine and 2 ml (23.86 mmol) of pyrrolidine in 30 ml of dimethylformamide is heated at 100° C. for 4 hours. The reaction mixture is subsequently concentrated under reduced pressure and then taken up in 100 ml of water and extracted three times with 100 ml of ethyl acetate. The organic phases are combined, then washed twice with 50 ml of water then once with 50 ml of a saturated sodium chloride solution, dried over sodium sulfate and then concentrated under reduced pressure. 3.47 g of the expected compound are thus isolated in the form of an orangey powder.

$^1$H NMR (DMSO $D_6$), δ (ppm): 1.9 (m, 4H); 3.79 (m, 4H); 3.88 (s, 3H); 7.62 (s, 1H); 8.69 (s, 1H).

5.2 3-Methoxy-2-(pyrrolidin-1-yl)-4-aminopyridine (Compound Va)

A suspension of 3.4 g (15.54 mmol) of 3-methoxy-5-nitro-2-(pyrrolidin-1-yl)pyridine, obtained in step 5.1, and of 0.33 g of 10% palladium-on-charcoal in 40 ml of ethanol is stirred at 20° C. for 5 hours under 5.6 bar of hydrogen. The reaction mixture is subsequently filtered through a celite pad, concentrated under reduced pressure, and then purified by silica column chromatography, elution being carried out with a mixture of dichloromethane and methanol. 0.9 g of the expected compound is thus isolated, which compound will be used as it is in the rest of the synthesis.

$^1$H NMR (CDCl$_3$), δ (ppm): 2.5 (m, 4H); 3.23 (broad peak, 2H); 3.49 (m, 4H); 3.91 (s, 3H); 5.90 (s, 1H); 7.71 (s, 1H).

5.3 N-[5-Methoxy-6-(pyrrolidin-1-yl)pyridin-3-yl]-5-fluoro-1-(3-fluorobenzyl)-1H-indole-2-carboxamide (Compound no. 8)

A solution of 0.5 g (1.74 mmol) of 5-fluoro-1-(3-fluorobenzyl)-1H-indole-2-carboxylic acid, prepared in step 1.1, of 0.33 g (1.74 mmol) of N-(3-dimethylaminopropyl)-N'-ethylcarbodiimide and of 0.23 g (1.74 mmol) of N-1-hydroxybenzotriazole in 10 ml of dimethylformamide is stirred for 15 minutes at 20° C. 0.43 g (2.26 mmol) of the compound (Va) prepared in step 5.2 is then added to the reaction medium. The reaction mixture is subsequently stirred for 12 hours at 20° C. and then concentrated under reduced pressure, poured into 100 ml of water and extracted twice with 100 ml of ethyl acetate. The organic phases are combined, then washed twice with 50 ml of water and then once with 50 ml of a saturated sodium chloride solution, dried over sodium sulfate, and then concentrated under reduced pressure. The product obtained is purified by silica column chromatography, elution being carried out with a mixture of dichloromethane and methanol. 0.3 g of the expect compound is thus isolated.

Melting point: 172-174° C.

$^1$H NMR (DMSO D$_6$), δ (ppm): 1.85 (m, 4H); 3.61 (m, 4H); 3.78 (s, 3H); 5.91 (s, 2H); 6.91 (m, 2H); 7.07 (txd, 1H); 7.15 (txd, 1H); 7.31 (q, 1H); 7.4 (s, 1H); 7.58 (m, 3H); 8.08 (s, 1H); 10.3 (s, 1H).

EXAMPLE 6

Compound No. 16

N-[4-Methoxy-6-(pyrrolidin-1-yl)pyridin-3-yl]-5-fluoro-1-(3-fluorobenzyl)-1H-indole-2-carboxamide

6.1 4-Methoxy-5-nitro-2-(pyrrolidin-1-yl)pyridine

The process is carried out according to the method described in step 5.1, using 5.4 g (28.64 mmol) of 2-chloro-4-methoxy-5-nitropyridine (WO 03/080610) and 4.53 g (63 mmol) of pyrrolidine. The product obtained is, in this case, purified by silica column chromatography, elution being carried out with a mixture of heptane and ethyl acetate. 3 g of the expected product are thus isolated.

$^1$H NMR (DMSO D$_6$), δ (ppm): 2.17 (m, 4H); 3.65 (m, 4H); 4.07 (s, 3H); 5.79 (s, 1H); 8.98 (s, 1H).

6.2 4-Methoxy-2-(pyrrolidin-1-yl)-5-aminopyridine (Compound Vb)

The process is carried out according to the method described in 5.2, using 1.5 g (6.72 mmol) of 4-methoxy-5-nitro-2-(pyrrolidin-1-yl)pyridine, obtained in step 6.1, and 0.15 g of 10% palladium-on-charcoal. 1.25 g of the expected product are thus obtained.

$^1$H NMR (DMSO D$_6$), δ (ppm): 1.81 (m, 4H); 3.29 (m, 4H); 3.71 (s, 3H); 4.52 (broad peak, 2H); 6.61 (s, 1H); 7.16 (s, 1H).

6.3 N-[4-Methoxy-6-(pyrrolidin-1-yl)pyridin-3-yl]-5-fluoro-1-(3-fluorobenzyl)-1H-indole-2-carboxamide (Compound no. 16)

The process is carried out according to the method described in example 2, using 0.5 g (1.74 mmol) of 5-fluoro-1-(3-fluorobenzyl)-1H-indole-2-carboxylic acid (example 1.1) and 0.424 g (2.09 mmol) of 4-methoxy-2-(pyrrolidin-1-yl)-5-aminopyridine, obtained in step 6.1 (Compound Vb). 0.59 g of the expected product is thus isolated.

Melting point: 196-198° C.

$^1$H NMR (CDCl$_3$), δ(ppm): 2.01 (m, 4H); 3.49 (m, 4H); 3.91 (s, 3H); 5.86 (m, 3H); 6.79 (dxd 1H); 6.9 (m, 2H); 7.02 (m, 2H); 7.23 (m, 2H); 7.34 (dxd, 1H); 7.9 (m, 1H); 8.85 (s, 1H).

EXAMPLE 7

Compound No. 20

N-[6-(1-Oxypyrrolidin-1-yl)pyridin-3-yl]-5-fluoro-1-(3-fluorobenzyl)-1H-indole-2-carboxamide A solution of 0.5 g (1.16 mmol) of N-[6-(pyrrolidin-1-yl)pyridin-3-yl]-5-fluoro-1-(3-fluorobenzyl)-1H-indole-2-carboxamide (compound no. 2 prepared according to the method described in example 2) and of 0.31 g (1.27 mmol) of metachloroperbenzoic acid (70%) in 20 ml of dichloromethane is stirred at 20° C. for 24 hours. 100 ml of dichloromethane are added to the reaction mixture, which is then washed successively with 20 ml of a saturated sodium carbonate solution and then 3 times with 20 ml of water, dried over magnesium sulfate, and then concentrated under reduced pressure. The product obtained is then purified by silica column chromatography, elution being carried out with a mixture of dichloromethane and methanol. 0.23 g of the expected product is thus isolated.

Melting point: 140-143° C.

$^1$H NMR (DMSO D$_6$), δ (ppm): 2.1 (m, 2H); 2.35 (m, 2H); 3.31 (m, 2H); 4.08 (m, 2H); 5.91 (s, 2H); 6.9 (m, 2H); 7.04 (txd, 1H); 7.2 (txd, 1H); 7.32 (m, 1H); 7.51 (s, 1H); 7.62 (m, 2H); 8.41 (m, 2H); 8.8 (s, 1H); 10.91 (s, 1H)

EXAMPLE 8

Compound No. 21

N-[2-(Pyrrolidin-1-yl)pyrimidin-5-yl]-5-fluoro-1-(3-fluorobenzyl)-1H-indole-2-carboxamide The process is carried out according to the method described in example 2, using 5-fluoro-1-(3-fluorobenzyl)-1H-indole-2-carboxylic acid (example 1.1) and 2-(pyrrolidin-1-yl)-5-aminopyrimidine (US 20060281772).

Melting point: 220-222° C.

$^1$H NMR (DMSO D$_6$), δ (ppm): 1.97 (m, 4H); 3.51 (m, 4H); 5.89 (s, 2H); 6.91 (m, 2H); 7.05 (txd, 1H); 7.16 (txd, 1H); 7.31 (m, 1H); 7.40 (s, 1H); 7.57 (m, 2H); 8.61 (s, 2H); 10.32 (s, 1H).

EXAMPLE 9

Compound No. 27

N-[2-Methyl-6-(pyrrolidin-1-yl)pyridin-3-yl]-5-fluoro-1-(3-fluorobenzyl)-1H-indole-2-carboxamide

9.1 2-Methyl-6-(pyrrolidin-1-yl)-3-nitropyridine

A suspension of 0.5 g (2.9 mmol) of 6-chloro-3-nitro-2-picoline, of 0.73 ml (8.69 mmol) of pyrrolidine and of 0.8 g (5.79 mmol) of potassium carbonate is heated at 110° C. for 2 hours. The reaction mixture is subsequently concentrated under reduced pressure and then poured into 100 ml of water. A solid is recovered by filtration and is dried so as to obtain 0.55 g of the expected product in the form of a yellow solid which will be used as it is in the rest of the synthesis.

9.2 2-Methyl-6-(pyrrolidin-1-yl)-3-aminopyridine (Compound no. Vd)

The process is carried out according to the method described in step 5.2, using 0.55 g (2.65 mmol) of 2-methyl-6-(pyrrolidin-1-yl)-3-nitropyridine, prepared in step 9.1, and 0.1 g of 10% palladium-on-charcoal. 0.34 g of the expected product is thus obtained, which product will be used as it is in the rest of the synthesis.

$^1$H NMR (CDCl$_3$), δ (ppm): 1.89 (m, 4H); 2.23 (s, 3H); 2.98 (broad peak, 2H); 3.31 (m, 4H); 6.03 (d, 1H); 6.82 (d, 1H).

9.3 N-[2-Methyl-6-(pyrrolidin-1-yl)pyridin-3-yl]-5-fluoro-1-(3-fluorobenzyl)-1H-indole-2-carboxamide (Compound no. 27)

The process is carried out according to the method described in example 5.3, using 0.4 g (1.39 mmol) of 5-fluoro-1-(3-fluorobenzyl)-1H-indole-2-carboxylic acid (example 1.1) and 0.32 g (1.81 mmol) of 2-methyl-6-(pyrrolidin-1-yl)-3-aminopyridine (compound no. Vd), described in step 9.2. 0.3 g of the expected product is thus isolated.

Melting point: 213-214° C.

$^1$H NMR (DMSO D$_6$), δ (ppm): 1.92 (m, 4H); 2.21 (s, 3H); 3.49 (m, 4H); 5.88 (s, 2H); 6.29 (d, 1H); 6.87 (d, 1H); 6.92 (d, 1H); 7.05 (txd, 1H); 7.15 (txd, 1H); 7.38 (m, 2H); 7.39 (s, 1H); 7.52 (d, 1H); 7.67 (m, 1H); 9.91 (s, 1H).

EXAMPLE 10

Compound No. 24

N-[6-(3-Hydroxyazetidin-1-yl)pyridin-3-yl]-5-fluoro-1-(3-fluorobenzyl)-1H-indole-2-carboxamide

10.1 2-(3-Hydroxyazetidin-1-yl)-5-nitropyridine

The process is carried out according to the method described in step 5.1, using 7 g (42.83 mmol) of 2-chloro-5-nitropyridine and 5.75 g (51.4 mmol) of 3-azetidinol hydrochloride. In this case, 13 g (128.45 mmol) of triethylamine are also added. 8 g of the expected product are thus isolated.

Melting point: 175-176° C.

$^1$H NMR (DMSO D$_6$), δ (ppm): 3.85 (m, 2H); 4.36 (m, 2H); 4.62 (m, 1H); 5.88 (d, 1H); 6.4 (d, 1H); 8.18 (dxd, 1H); 8.92 (s, 1H).

10.2 2-(3-Hydroxyazetidin-1-yl)-5-aminopyridine (Compound Ve)

The process is carried out according to the method described in step 5.2, using 5.5 g (28.18 mmol) of 2-(3-hydroxyazetidin-1-yl)-5-nitropyridine, prepared in step 10.1, and 0.5 g of 10% palladium-on-charcoal. 4.5 g of the expected product are thus obtained in the form of violet crystals.

Melting point: 148-150° C.

$^1$H NMR (DMSO D$_6$), δ (ppm): 3.49 (m, 2H); 3.98 (m, 2H); 4.48 (broad peak, 3H); 5.48 (broad peak, 1H); 6.22 (d, 1H); 6.91 (d, 1H); 7.58 (s, 1H).

10.3 N-[6-(3-Hydroxyazetidin-1-yl)pyridin-3-yl]-5-fluoro-1-(3-fluorobenzyl)-1H-indole-2-carboxamide (Compound no. 24)

The process is carried out according to the method described in example 2, using 0.5 g (1.74 mmol) of 5-fluoro-1-(3-fluorobenzyl)-1H-indole-2-carboxylic acid (example 1.1) and 0.35 g (2.09 mmol) of 2-(3-hydroxyazetidin-1-yl)-5-aminopyridine, obtained in step 10.2 (Compound Ve).

Melting point: 199-200° C.

$^1$H NMR (DMSO D$_6$), δ(ppm): 3.67 (m, 2H); 4.13 (m, 2H); 4.58 (m, 1H); 5.61 (m, 1H); 5.91 (s, 2H); 6.42 (d, 1H); 6.91 (m, 2H); 7.05 (m, 1H); 7.18 (txd, 1H); 7.36 (m, 1H); 7.42 (s, 1H); 7.58 (m, 2H); 7.88 (dxd, 1H); 8.39 (s, 1H); 10.35 (s, 1H).

EXAMPLE 11

Compound No. 53

N-[6-(Pyrrolidin-1-yl)-4-(trifluoromethyl)pyridin-3-yl]-5-fluoro-1-(3-fluorobenzyl)-1H-indole-2-carboxamide

11.1 Methyl 6-(pyrrolidin-1-yl)-4-(trifluoromethyl)pyridine-3-carboxylate

A mixture of 2.5 g (10.43 mmol) of methyl 6-chloro-4-trifluoromethylnicotinate, of 2.88 g (20.87 mmol) of potassium carbonate and of 2.61 ml (31.3 mmol) of pyrrolidine in 90 ml of dimethylformamide is heated at 100° C. for 3 hours. The reaction mixture is subsequently concentrated under reduced pressure and then taken up in 100 ml of water. A precipitate is recovered by filtration and is washed with 150 ml of water. After drying under reduced pressure, 2.5 g of the expected product are isolated.

$^1$H NMR (CDCl$_3$), δ (ppm): 2.11 (m, 4H); 3.61 (broad peak, 4H); 3.93 (s, 3H); 6.69 (s, 1H); 8.89 (s, 1H).

11.2 6-(Pyrrolidin-1-yl)-4-(trifluoromethyl)pyridine-3-carboxylic Acid

A mixture of 2.5 g (9.12 mmol) of methyl 6-(pyrrolidin-1-yl)-4-(trifluoromethyl)pyridine-3-carboxylate, obtained in step 11.1, and of 0.76 g (13.67 mmol) of potassium hydroxide in 50 ml of methanol and 2 ml of water is stirred for 24 hours at 20° C. The mixture is subsequently concentrated under reduced pressure. 100 ml of water are subsequently added and the solution is washed with 100 ml of dichloromethane and then acidified to pH 4 by the addition of concentrated hydrochloric acid. A precipitate is recovered by filtration and is washed with 50 ml of water. After drying under reduced pressure, 2.2 g of the expected compound are isolated.

11.3 6-(Pyrrolidin-1-yl)-4-trifluoromethyl-3-(tert-butoxycarbonylamino)pyridine A mixture of 2.2 g (8.45 mmol) of 6-(pyrrolidin-1-yl)-4-(trifluoromethyl)pyridine-3-carboxylic acid, obtained in step 11.2, of 2.37 ml (10.99 mmol) of diphenylphosphorylazide and of 2.95 ml (21.14 mmol) of triethylamine in 25 ml of tert-butanol is heated for 5 hours at 90° C. The reaction mixture is subsequently concentrated under reduced pressure, taken up with 50 ml of water, and then extracted 3 times with 50 ml of dichloromethane. The organic phases are combined, washed with 50 ml of water, dried over sodium sulfate, and then concentrated under reduced pressure. The oil obtained is purified by silica column chromatography, elution being carried out with a mixture of dichloromethane and methanol. 1.05 g of the expected product are thus isolated.

$^1$H NMR (CDCl$_3$), δ (ppm): 1.53 (s, 9H); 2.09 (m, 4H); 3.51 (m, 4H); 6.2 (broad peak, 1H); 6.52 (s, 1H); 8.39 (broad peak, 1H).

11.4 6-(Pyrrolidin-1-yl)-4-trifluoromethyl-3-aminopyridine hydrochloride (Amine Vg)

A solution of 1 g (3.02 mmol) of 6-(pyrrolidin-1-yl)-4-trifluoromethyl-3-(tert-butoxycarbonylamino)pyridine, prepared in step 11.3, in 11 ml of 4N hydrochloric acid in dioxane is stirred for 5 hours at reflux. 200 ml of ethyl ether are subsequently added to the cooled reaction mixture. 0.8 g of a precipitate is recovered by filtration.

Melting point: 207-209° C.;
$^1$H NMR (DMSO D$_6$), δ (ppm): 2 (m, 4H); 3.52 (m, 4H); 7.1 (s, 1H); 7.49 (broad peak, 2H); 7.92 (s, 1H).

11.5 N-[6-(Pyrrolidin-1-yl)-4-trifluoromethylpyridin-3-yl]-5-fluoro-1-(3-fluorobenzyl)-1H-indole-2-carboxamide (Compound no. 53)

The process is carried out according to the method described in step 5.3, using 0.3 g (1.04 mmol) of 5-fluoro-1-(3-fluorobenzyl)-1H-indole-2-carboxylic acid (example 1.1), and of 0.363 g (1.36 mmol) of 6-(pyrrolidin-1-yl)-4-trifluoromethyl-3-aminopyridine hydrochloride, prepared in step 11.4, in the presence of 0.22 ml (1.57 mmol) of triethylamine.

Melting point: 170-171° C.;
$^1$H NMR (DMSO D$_6$), δ (ppm): 1.99 (m, 4H); 3.49 (m, 4H); 5.87 (s, 2H); 6.7 (s, 1H); 6.86-7.22 (m, 4H); 7.31 (m, 1H); 7.4 (s, 1H); 7.57 (dxd, 1H); 7.65 (m, 1H); 8.11 (s, 1H).

EXAMPLE 12

Compound No. 28

N-[6-(3-Azabicyclo[3.1.0]hex-3-yl)pyridin-3-yl]-5-fluoro-1-(3-fluorobenzyl)-1H-indole-2-carboxamide

12.1 2-(3-Azabicyclo[3.1.0]hex-3-yl)-5-nitropyridine

A suspension of 0.2 g (1.26 mmol) of 2-chloro-5-nitropyridine, of 0.166 g (1.39 mmol) of 3-azabicyclo[3.1.0]hexane (*Bioorg. &Med. Chem. Lett.* 2005, 15(8) 2093) and of 0.52 g (3.78 mmol) of potassium carbonate in 5 ml of dimethylformamide is stirred at ambient temperature for 36 hours. The mixture is subsequently poured into 5 ml of water and then extracted 3 times with 20 ml of ethyl acetate. The organic phases are subsequently combined, dried over magnesium sulfate, and then concentrated under reduced pressure. 0.22 g of the expected product is thus obtained, which product is used as it is in the rest of the synthesis.

12.2 2-(3-Azabicyclo[3.1.0]hex-3-yl)-5-aminopyridine (Vf)

The process is carried out according to the method used in example 5.2, using 0.2 g (0.97 mol) of 2-(3-azabicyclo[3.1.0]hex-3-yl)-5-nitropyridine, described in step 12.1, and 0.5 g of 10% palladium-on-charcoal. 0.1 g of the expected product is thus isolated, which product will be used as it is in the next step.

$^1$H NMR (DMSO D$_6$), δ (ppm): 0.2 (m, 1H); 0.66 (m, 1H); 1.6 (m, 2H); 3.11 (m, 2H); 3.51 (d, 2H); 4.32 (broad peak, 2H); 6.25 (d, 1H); 6.99 (d, 1H); 7.55 (s, 1H).

12.3 N-[6-(3-Azabicyclo[3.1.0]hex-3-yl)pyridin-3-yl]-5-fluoro-1-(3-fluorobenzyl)-1H-indole-2-carboxamide (Compound no. 28).

The process is carried out according to the method described in example 2, using 0.15 g (0.52 mmol) of 5-fluoro-1-(3-fluorobenzyl)-1H-indole-2-carboxylic acid and 0.1 g (0.57 mmol) of 2-(3-azabicyclo[3.1.0]hex-3-yl)-5-aminopyridine, prepared in step 12.2. 0.17 g of the expected product is thus isolated.

Melting point: 193-195° C.
$^1$H NMR (DMSO D$_6$), δ (ppm): 0.02 (m, 1H); 0.51 (m, 1H); 1.47 (m, 2H); 3.41 (d, 2H); 5.67 (s, 2H); 6.25 (d, 1H); 6.69 (m, 2H); 6.83 (m, 1H); 6.93 (m, 1H); 7.1 (m, 1H); 7.15 (s, 1H); 7.31 (dxd, 1H); 7.39 (m, 1H); 7.6 (m, 1H); 8.11 (s, 1H); 10.03 (s, 1H).

EXAMPLE 13

Compound No. 29

N-[6-(3-Hydroxyazetidin-1-yl)pyridin-3-yl]-1-(3-fluorobenzyl)-5-trifluoromethyl-1H-indole-2-carboxamide The process is carried out according to the method described in example 2, using 5-trifluoromethyl-1-(3-fluorobenzyl)-1H-indole-2-carboxylic acid (WO 2006/072736) and 2-(3-hydroxyazetidin-1-yl)-5-aminopyridine, prepared in step 10.2 of example 10 (Compound Ve).

Melting point: 194-196° C.
$^1$H NMR (DMSO D$_6$), δ (ppm): 3.68 (m, 2H); 4.17 (m, 2H); 4.59 (m, 1H); 5.6 (d, 1H); 5.93 (s, 2H); 6.42 (d, 1H); 6.91 (m, 2H); 7.09 (txd, 1H); 7.32 (m, 1H); 7.55 (m, 2H); 7.79 (d, 1H); 7.88 (d, 1H); 8.2 (s, 1H); 8.38 (s, 1H); 10.41 (s, 1H).

EXAMPLE 14

Compound No. 30

N-[6-(3-Hydroxyazetidin-1-yl)pyridin-3-yl]-1-(3-fluorobenzyl)-6-trifluoromethyl-1H-indole-2-carboxamide The process is carried out according to the method described in example 2, using 6-trifluoromethyl-1-(3-fluorobenzyl)-1H-indole-2-carboxylic acid and 2-(3-hydroxyazetidin-1-yl)-5-aminopyridine, prepared in step 10.2 of example 10 (Compound Ve).

Melting point: 253-255° C.

$^1$H NMR (DMSO D$_6$), δ (ppm): 3.67 (m, 2H); 4.17 (m, 2H); 4.59 (m, 1H); 5.6 (d, 1H); 6.0 (s, 2H); 6.42 (d, 1H); 6.91 (m, 2H); 7.09 (txd, 1H); 7.36 (m, 1H); 7.47 (d, 1H); 7.51 (s, 1H); 7.85 (d, 1H); 7.99 (d, 1H); 8.06 (s, 1H); 8.33 (s, 1H); 10.41 (s, 1H).

EXAMPLE 15

Compound No. 23

N-[6-(Pyrrolidin-1-yl)pyridin-3-yl]-1-[(pyridin-4-yl)methyl]-5-fluoro-1H-indole-2-carboxamide

15.1 5-Fluoro-1-[(pyridin-4-yl)methyl]-1H-indole-2-carboxylic Acid

A solution of 2.1 g (7.04 mmol) of ethyl 5-fluoro-1-[(pyridin-4-yl)methyl]-1H-indole-2-carboxylate (WO 2007/010144) and of 1.18 g (21.12 mmol) of potassium hydroxide in 80 ml of ethanol and 2 ml of water is refluxed for 2 hours. The reaction mixture is subsequently concentrated under reduced pressure. 100 ml of water are added and the pH of the solution is brought to pH 8 by the addition of a concentrated hydrochloric acid solution. A precipitate is recovered by filtration and is washed with water and then dried under reduced pressure. 1.5 g of the expected product are thus obtained.

Melting point: 282-283° C.

15.2 N-[6-Chloropyridin-3-yl]-5-fluoro-1-[(pyridin-4-yl)methyl]-1H-indole-2-carboxamide The process is carried out according to the method described in example 2, using 0.7 g (2.59 mmol) of 5-fluoro-1-[(pyridin-4-yl)methyl]-1H-indole-2-carboxylic acid, obtained in step 15.1, and 0.4 g (3.11 mmol) of 2-chloro-5-aminopyridine. 0.41 g of expected product is isolated.

Melting point: 244-246° C.

15.3 N-[6-(pyrrolidin-1-yl)pyridin-3-yl]-1-[(pyridin-4-yl)methyl]-5-fluoro-1H-indole-2-carboxamide (Compound no. 23)

The process is carried out according to the method described in example 3.2, using 0.4 g (1.05 mmol) of N-[6-chloropyridin-3-yl]-5-fluoro-1-[(pyridin-4-yl)methyl]-1H-indole-2-carboxamide, obtained in step 15.2, and 2.63 ml (31.51 mmol) of pyrrolidine. 0.24 g of the expected product is isolated.

Melting point: 255-257° C.

$^1$H NMR (DMSO D$_6$), δ (ppm): 1.92 (m, 4H); 3.38 (m, 2H); 5.92 (s, 4H); 6.45 (d, 1H); 7.0 (d, 2H); 7.16 (txd, 1H); 7.43 (s, 1H); 7.57 (m, 2H); 7.81 (m, 1H); 8.31 (s, 1H); 8.48 (d, 2H); 10.22 (s, 1H).

EXAMPLE 16

Compound No. 14

N-[6-(pyrrolidin-1-yl)pyridin-3-yl]-1-[(pyridin-4-yl)methyl]-5-trifluoromethyl-1H-indole-2-carboxamide

16.1 5-Trifluoromethyl-1-[(pyridin-4-yl)methyl]-1H-indole-2-carboxylic acid The process is carried out according to the method described in example 15.1, using ethyl 5-trifluoromethyl-1-[(pyridin-4-yl)methyl]-1H-indole-2-carboxylate (WO 07/010,144). The product obtained is used as it is in the rest of the synthesis.

16.2 N-[6-Chloropyridin-3-yl]-1-[(pyridin-4-yl)methyl]-5-trifluoromethyl-1H-indole-2-carboxamide The process is carried out according to the method described in example 3.1, using 0.5 g (1.56 mmol) of 5-trifluoromethyl-1-[(pyridin-4-yl)methyl]-1H-indole-2-carboxylic acid, prepared in step 16.1, and 0.22 g (1.72 mmol) of 2-chloro-5-aminopyridine. 0.5 g of the expected product is isolated by this method, which product is used as it is in the rest of the synthesis.

16.3 N-[6-(Pyrrolidin-1-yl)pyridin-3-yl]-1-[(pyridin-4-yl)methyl]-5-trifluoromethyl-1H-indole-2-carboxamide (Compound no. 14)

The process is carried out according to the method described in example 4, using 0.5 g (1.16 mmol) of N-[6-chloropyridin-3-yl]-1-[(pyridin-4-yl)methyl]-5-trifluoromethyl-1H-indole-2-carboxamide, obtained in step 16.2, and 2.91 ml (34.82 mmol) of pyrrolidine. The mixture is placed in a pressurized tube which is heated for 50 minutes at 170° C. under 200 watts, by means of a microwave oven. The mixture is subsequently concentrated under reduced pressure, and taken up with 100 ml of ethyl acetate. The organic phase is subsequently washed twice with 30 ml of water and then once with a saturated sodium chloride solution, dried over magnesium sulfate, and then concentrated under reduced pressure. The product obtained is purified by silica column chromatography, elution being carried out with a mixture of dichloromethane and methanol. 0.24 g of the expected product is thus isolated.

Melting point: 248-250° C.

$^1$H NMR (DMSO D$_6$), δ (ppm): 1.95 (m, 4H); 3.41 (m, 4H); 5.98 (s, 2H); 6.45 (d, 1H); 7.03 (d, 2H); 7.59 (m, 2H); 7.73 (d, 1H); 7.81 (d, 1H); 8.19 (s, 1H); 8.32 (s, 1H); 8.49 (d, 2H).

EXAMPLE 17

Compound No 22

N-[6-(3-Azabicyclo[3.2.0]hept-3-yl)pyridin-3-yl]-5-fluoro-1-(3-fluorobenzyl)-1H-indole-2-carboxamide A mixture of 0.2 g (0.5 mmol) of N-[6-chloropyridin-3-yl]-5-fluoro-1-(3-fluorobenzyl)-1H-indole-2-carboxamide, prepared in step 3.1, of 0.0806 g (0.6 mmol) of 3-azabicyclo [3.2.0]heptane (*J. Med. Chem.* 1967, 10(4), 621) and of 0.0564 g (1.01 mmol) of potassium hydroxide in 0.5 ml of N-methylpyrrolidinone is heated for 90 minutes in a microwave oven regulated at 150° C. under 150 watts. The reaction mixture is subsequently poured into 20 ml of water. The mixture is extracted with three times 30 ml of ethyl acetate. The combined organic phases are washed with 30 ml of water, dried over sodium sulfate, and then concentrated under reduced pressure. The resulting solid is subsequently purified by silica column chromatography, elution being carried out with a mixture of n-heptane and ethyl acetate. 35 mg of the expected product are thus isolated.

Melting point: 163-165° C.

$^1$H NMR (DMSO D$_6$), δ (ppm): 1.71 (m, 2H); 2.23 (m, 2H); 3.02 (m, 2H); 3.2 (m, 2H); 3.63 (d, 2H); 5.9 (s, 2H); 6.62 (d, 1H); 6.91 (m, 2H); 7.05 (txd, 1H); 7.16 (txd, 1H); 7.33 (m, 1H); 7.4 (s, 1H); 7.54 (dxd, 1H); 7.6 (m, 1H); 7.88 (dxd, 1H); 8.4 (s, 1H); 10.3 (s, 1H).

Table 2 which follows illustrates the chemical structures and the physical properties of some compounds of formula (I) according to the invention.

In this table:

- the "Mp" column gives the melting points of the products in degrees Celsius (° C.);
- in the "salt/base" column, "—" represents a compound in the form of a free base, whereas "HCl" represents a compound in hydrochloride form and the ratio between parentheses is the (acid:base) ratio;
- "t-Bu" corresponds to a tert-butyl group, "iPr" to an isopropyl group, "et" to an ethyl group.

TABLE 2

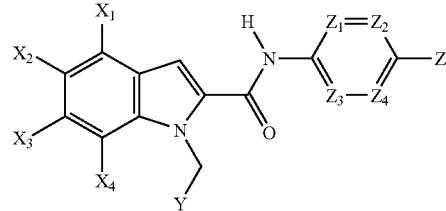

(I)

| No. | $X_1, X_2, X_3, X_4$ | Y | $Z_1, Z_2, Z_3, Z_4$ | Z | Salt/base | Mp (° C.) |
|---|---|---|---|---|---|---|
| 1 | H, F, H, H | 3-fluorophenyl | CH, CH, CH, N | (R)-N-(3-tert-butoxy carbonylamino) pyrrolidinyl | — | 207-209 |
| 2 | H, F, H, H | 3-fluorophenyl | CH, CH, CH, N | pyrrolidinyl | — | 199-201 |
| 3 | H, F, H, H | 3-fluorophenyl | CH, CH, CH, N | (R)-3-amino-pyrrolidinyl | — | 192-194 |
| 4 | H, F, H, H | 3-fluorophenyl | CH, CH, CH, N | azetidinyl | — | 227-228 |
| 5 | H, CF$_3$, H, H | 3-fluorophenyl | CH, CH, CH, N | pyrrolidinyl | — | 185-186 |
| 6 | H, F, H, H | 3-fluorophenyl | C—CH$_3$, CH, CH, N | pyrrolidinyl | — | 176-178 |
| 7 | H, F, H, H | 3-fluorophenyl | CH, CH, CH, N | 3-hydroxypyrrolidinyl | — | 229-230 |
| 8 | H, F, H, H | 3-fluorophenyl | CH, C—OCH$_3$, CH, N | pyrrolidinyl | — | 172-174 |
| 9 | H, H, CF$_3$, H | Pyridin-4-yl | CH, CH, CH, N | pyrrolidinyl | — | 261-262 |
| 10 | H, F, H, H | Pyridin-4-yl | C—CH$_3$, CH, CH, N | pyrrolidinyl | — | 115-120 |
| 11 | H, F, H, H | Pyridin-4-yl | CH, C—OCH$_3$, CH, N | pyrrolidinyl | — | 213-215 |
| 12 | H, F, H, H | 3-(pyrrolidin-1yl)phenyl | CH, CH, CH, N | pyrrolidinyl | — | 225-227 |
| 13 | H, F, H, H | 3-fluorophenyl | CH, CH, CH, N | piperidinyl | — | 190-192 |
| 14 | H, CF$_3$, H, H | Pyridin-4-yl | CH, CH, CH, N | pyrrolidinyl | — | 248-250 |
| 15 | H, F, H, H | 6-methylpyridin-2-yl | CH, CH, CH, N | pyrrolidinyl | — | 241-243 |
| 16 | H, F, H, H | 3-fluorophenyl | C—OCH$_3$, CH, CH, N | pyrrolidinyl | — | 196-198 |
| 17 | H, F, H, H | 3-fluorophenyl | CH, CH, CH, N | morpholinyl | HCl (1:1) | 246-250 |
| 18 | H, F, H, H | Pyridin-4-yl | C—OCH$_3$, CH, CH, N | pyrrolidinyl | — | 225-226 |
| 19 | H, F, H, H | 2-methylpyridin-4-yl | CH, CH, CH, N | pyrrolidinyl | — | 213-215 |
| 20 | H, F, H, H | 3-fluorophenyl | CH, CH, CH, N | 1-oxypyrrolidinyl | — | 140-143 |
| 21 | H, F, H, H | 3-fluorophenyl | CH, N, CH, N | pyrrolidinyl | — | 220-222 |
| 22 | H, F, H, H | 3-fluorophenyl | CH, CH, CH, N | 3-azabicyclo[3.2.0]heptyl | — | 163-165 |
| 23 | H, F, H, H | Pyridin-4-yl | CH, CH, CH, N | pyrrolidinyl | — | 255-257 |
| 24 | H, F, H, H | 3-fluorophenyl | CH, CH, CH, N | 3-hydroxy-azetidinyl | — | 199-200 |
| 25 | H, CF$_3$, H, H | 3-fluorophenyl | CH, CH, CH, N | azetidinyl | — | 222-224 |
| 26 | H, F, H, H | Pyridin-4-yl | CH, CH, CH, N | azetidinyl | — | 212-214 |
| 27 | H, F, H, H | 3-fluorophenyl | CH, CH, C—CH$_3$, N | pyrrolidinyl | — | 213-214 |
| 28 | H, F, H, H | 3-fluorophenyl | CH, CH, CH, N | 3-azabicyclo[3.1.0]hexyl | — | 193-195 |
| 29 | H, CF$_3$, H, H | 3-fluorophenyl | CH, CH, CH, N | 3-hydroxy-azetidinyl | — | 194-196 |
| 30 | H, H, CF$_3$, H | 3-fluorophenyl | CH, CH, CH, N | 3-hydroxy-azetidinyl | — | 253-255 |
| 31 | H, F, H, H | phenyl | CH, CH, CH, N | azetidinyl | — | 208-210 |

TABLE 2-continued (I)

| No. | $X_1, X_2, X_3, X_4$ | Y | $Z_1, Z_2, Z_3, Z_4$ | Z | Salt/base | Mp (° C.) |
|---|---|---|---|---|---|---|
| 32 | CH$_3$, H, CH$_3$, H | 3-fluorophenyl | CH, CH, CH, N | azetidinyl | — | 234-236 |
| 33 | H, H, t-Bu, H | 3-fluorophenyl | CH, CH, CH, N | azetidinyl | — | 204-206 |
| 34 | H, H, O-iPr, H | 3-fluorophenyl | CH, CH, CH, N | azetidinyl | — | 198-200 |
| 35 | H, SO$_2$CH$_3$, H, H | 3-fluorophenyl | CH, CH, CH, N | azetidinyl | — | 258-260 |
| 36 | H, H, N(CH$_3$)$_2$, H | 3-fluorophenyl | CH, CH, CH, N | azetidinyl | — | 256-258 |
| 37 | H, H, SCH$_3$, H | 3-fluorophenyl | CH, CH, CH, N | azetidinyl | — | 206-208 |
| 38 | F, H, H, H | 3-fluorophenyl | CH, CH, CH, N | azetidinyl | — | 214-216 |
| 39 | H, H, H, F | 3-fluorophenyl | CH, CH, CH, N | azetidinyl | — | 244-246 |
| 40 | H, H, F, H | 3-fluorophenyl | CH, CH, CH, N | azetidinyl | — | 210-212 |
| 41 | Cl, H, H, H | 3-fluorophenyl | CH, CH, CH, N | azetidinyl | — | 226-228 |
| 42 | H, H, Cl, H | 3-fluorophenyl | CH, CH, CH, N | azetidinyl | — | 218-220 |
| 43 | H, Cl, H, H | 3-fluorophenyl | CH, CH, CH, N | azetidinyl | — | 226-228 |
| 44 | H, H, H, H | 3-fluorophenyl | CH, CH, CH, N | azetidinyl | — | 328-330 |
| 45 | CH$_3$, H, H, H | 3-fluorophenyl | CH, CH, CH, N | azetidinyl | — | 246-248 |
| 46 | H, H, CH$_3$, H | 3-fluorophenyl | CH, CH, CH, N | azetidinyl | — | 228-230 |
| 47 | H, CH$_3$, H, H | 3-fluorophenyl | CH, CH, CH, N | azetidinyl | — | 236-238 |
| 48 | H, iPr, H, H | 3-fluorophenyl | CH, CH, CH, N | azetidinyl | — | 204-206 |
| 49 | H, t-Bu, H, H | 3-fluorophenyl | CH, CH, CH, N | azetidinyl | — | 212-214 |
| 50 | H, H, Et, H | 3-fluorophenyl | CH, CH, CH, N | azetidinyl | — | 196-198 |
| 51 | H, H, iPr, H | 3-fluorophenyl | CH, CH, CH, N | azetidinyl | — | 184-186 |
| 52 | H, H, CF$_3$, H | 3-fluorophenyl | CH, CH, CH, N | azetidinyl | — | 220-222 |
| 53 | H, F, H, H | 3-fluorophenyl | C—CF$_3$, CH, CH, N | pyrrolidinyl | — | 170-171 |

The NMR data of certain compounds of the table are subsequently described, by way of examples.

Compound no. 25:
$^1$H NMR (DMSO D$_6$), δ (ppm): 2.31 (m, 2H); 3.92 (t, 4H); 5.92 (s, 2H); 6.4 (d, 1H); 6.94 (m, 2H); 7.09 (txd, 1H); 7.37 (m, 1H); 7.57 (m, 2H); 7.79 (d, 1H); 7.87 (dxd, 1H); 8.2 (s, 1H); 8.36 (d, 2H); 10.41 (s, 1H).

Compound no. 26:
$^1$H NMR (DMSO D$_6$), δ (ppm): 2.32 (m, 2H); 3.92 (t, 4H); 5.91 (s, 2H); 6.38 (d, 1H); 6.99 (d, 2H); 7.15 (txd, 1H); 7.41 (s, 1H); 7.57 (m, 2H); 7.81 (m, 1H); 8.43 (m, 1H); 8.46 (d, 2H); 10.4 (s, 1H).

Compound no. 35:
$^1$H NMR (DMSO D$_6$), δ (ppm): 2.32 (m, 2H); 3.21 (s, 3H); 3.92 (t, 4H); 5.98 (s, 2H); 6.4 (d, 1H); 6.92 (d, 2H); 7.09 (txd, 1H); 7.35 (m, 1H); 7.6 (s, 1H); 7.81 (m, 3H); 8.39 (m, 2H); 10.42 (s, 1H).

Compound no. 38:
$^1$H NMR (DMSO D$_6$), δ (ppm): 2.31 (m, 2H); 3.92 (t, 4H); 5.92 (s, 2H); 6.4 (d, 1H); 6.93 (m, 3H); 7.08 (txd, 1H); 7.31 (m, 2H); 7.41 (m, 1H); 7.61 (s, 1H); 7.86 (dxd, 1H); 8.38 (s, 1H); 10.3 (s, 1H).

Compound no. 40:
$^1$H NMR (DMSO D$_6$), δ (ppm): 2.31 (m, 2H); 3.90 (t, 4H); 5.89 (s, 2H); 6.4 (d, 1H); 6.91 (m, 2H); 7.06 (m, 2H); 7.33 (m, 1H); 7.41 (s, 1H); 7.47 (dxd, 1H); 7.78 (m, 1H); 7.86 (m, 1H); 8.35 (s, 1H); 10.23 (s, 1H).

Compound no. 45:
$^1$H NMR (DMSO D$_6$), δ (ppm): 2.31 (m, 2H); 2.56 (s, 3H); 3.91 (t, 4H); 5.9 (s, 2H); 6.4 (d, 1H); 6.91 (m, 3H); 7.04 (txd, 1H); 7.18 (m, 1H); 7.31 (m, 2H); 7.49 (s, 1H); 7.88 (m, 1H); 8.38 (s, 1H); 10.25 (s, 1H).

Compound no. 46:
$^1$H NMR (DMSO D$_6$), δ (ppm): 2.31 (m, 2H); 2.41 (s, 3H); 3.91 (t, 4H); 5.85 (s, 2H); 6.4 (d, 1H); 6.82-7.09 (m, 4H); 7.35 (m, 3H); 7.61 (d, 1H); 7.83 (dxd, 1H); 8.36 (s, 1H); 10.21 (s, 1H).

Compound no. 47:
$^1$H NMR (DMSO D$_6$), δ (ppm): 2.29 (m, 2H); 2.4 (s, 3H); 3.91 (t, 4H); 5.89 (s, 2H); 6.39 (d, 1H); 6.82-6.91 (m, 2H); 7.02 (txd, 1H); 7.12 (dxd, 1H); 7.31 (m, 2H); 7.41 (d, 1H); 7.51 (s, 1H); 7.87 (dxd, 1H); 8.34 (s, 1H); 10.23 (s, 1H).

Compound no. 49:
$^1$H NMR (DMSO D$_6$), δ (ppm): 1.32 (s, 9H); 2.3 (m, 2H); 3.91 (t, 4H); 5.85 (s, 2H); 6.38 (d, 1H); 6.92 (m, 2H); 7.03 (txd, 1H); 7.35 (m, 4H); 7.66 (s, 1H); 7.85 (dxd, 1H); 8.43 (s, 1H); 10.19 (s, 1H).

Compound no. 52:
$^1$H NMR (DMSO D$_6$), δ (ppm): 2.31 (m, 2H); 3.91 (t, 4H); 6 (s, 2H); 6.39 (d, 1H); 6.91 (m, 2H); 7.07 (txd, 1H); 7.32 (m, 1H); 7.45 (d, 1H); 7.49 (s, 1H); 7.82 (dxd, 1H); 7.92 (d, 1H); 8.02 (s, 1H); 8.34 (s, 1H); 10.41 (s, 1H).

The compounds of the invention were subjected to in vitro and in vivo pharmacological assays which demonstrated their advantage as substances with therapeutic activities.

The compounds of the invention also have characteristics of water-solubility which provides good activity in vivo.

Test for Inhibition of the Current Induced by Capsaicin on Rat DRGs

Primary culture of rat dorsal root ganglion (DRG) cells:

The neurons of the DRG naturally express the TRPV1 receptor.

Newborn rat DRG primary cultures are prepared from one-day-old rat pups. Briefly, after dissection, the ganglia are trypsinized and the cells are mechanically dissociated by controlled trituration. The cells are resuspended in an Eagle's basal culture medium containing 10% of foetal calf serum, 25 mM KCl, 2 mM glutamine, 100 μg/ml gentamycin and 50 ng/ml of NGF, and then deposited onto laminin-coated glass cover slips ($0.25 \times 10^6$ cells per cover slip) which are then placed in 12-well Corning dishes. The cells are incubated at 37° C. in a humidified atmosphere containing 5% $CO_2$ and 95% air. Cytosine-β-arabinoside (1 μM) is added 48 h after placing in culture, in order to prevent the development of non-neuronal cells. The cover slips are transferred into the experimental chambers for the patch-clamp studies after 7-10 days of culture.

Electrophysiology:

The measuring chambers (volume 800 μl) containing the cell preparation are placed on the platform of an inverted microscope (Olympus IMT2) equipped with Hoffman optics (Modulation Contrast, New York) and observed at the magnification of ×400. The chambers are continually perfused by gravity (2.5 ml/min) by means of a solution distributing device with 8 inlets, and the sole outlet of which, consisting of a polyethylene tube (500 μm aperture), is placed at least 3 mm from the cell studied. The "whole cell" configuration of the patch-clamp technique was used. The borosilicate glass pipettes (resistance 5-10 MOhms) are moved close to the cell by means of a 3D piezoelectric micromanipulator (Burleigh, PC1000). The overall currents (membrane potential fixed at −60 mV) are recorded with an Axopatch 1 D amplifier (Axon Instruments, Foster city, Calif.), connected to a PC control by Pclamp8 software (Axon Instrument). The current traces are recorded on paper and simultaneously digitized (sampling frequency 15 to 25 Hz) and acquired on the hard drive of the PC.

The application of a micromolar solution of capsaicin causes, on the DRG cells (voltage fixed at −70 mV), an inward cationic current. In order to minimize the desensitization of the receptors, a minimum period of one minute is observed between two applications of capsaicin. After a controlled period (stabilization of the capsaicin response alone), the compounds to be tested are applied alone at a given concentration (concentration of 10 nM or of 0.1 nM) for a period of 4 to 5 minutes, during which several capsaicin+compound tests are carried out (obtaining of maximum inhibition). The results are expressed as % inhibition of the control capsaicin response.

The percentages of inhibition of the capsaicin response (1 microM) are between 20% and 100% for the most active compounds of the invention tested at concentrations of 10 nM to 0.1 nM (see examples in table 3).

The compounds of the invention are therefore effective antagonists, in vitro, of TRPV1-type receptors.

TABLE 3

| Compound no. | % inhibition in DRG patch |
|---|---|
| 2 | 46% (1 nM) |
| 4 | 89% (1 nM) |
| 7 | 85% (10 nM) |
| 21 | 79% (10 nM) |

Mouse Corneal Irritation Test

The irritant nature of capsaicin can be readily assessed at the level of the cornea since this organ is one of the most innervated by C fibres. In this context, according to preliminary experiments, the application of a very small amount of capsaicin (2 μl at a concentration of 160 μM) to the surface of the cornea of an animal results in a certain number of stereotyped behaviors associated with the irritation and that can be readily listed. Among these are: blinking of the eye, rubbing of the instilled eye with the ipsilateral forelimb, rubbing of the face with both forelimbs, scratching of the ipsilateral face with the hind limb. The duration of these behaviors does not exceed the 2 minutes of observation and the animal then returns to its normal activity. Its appearance is, moreover, also normal. The mouse is not hidden away in a corner with its coat bristling and does not develop any observable signs of suffering. It can be concluded from this that the duration of action of capsaicin at these doses is less than 2 minutes.

Summary of the Methodology:

The principle of the series of experiments is to determine whether the compounds of the invention can influence the behavioral response induced via a given amount of capsaicin. The capsaicin is initially diluted to 25 mM in DMSO and diluted, for its final use, in physiological saline with 10% Tween 80. It appears, based on control studies, that, under these conditions, the solvent has no effect.

In practice, the product to be tested, prepared at 25 mM in DMSO and diluted for its final use in physiological serum with 10% Tween 80, at the highest concentration of 500 μM, is administered by local application to the surface of the cornea in a volume of 2 μl, 10 minutes before the application of the capsaicin. The animal receives the ocular instillation of 2 μl of a solution of capsaicin at 160 μM prepared as indicated above. Over the course of a period of observation of 2 minutes following the instillation, the number of times the instilled eye is rubbed by the ipsilateral forelimb is counted for each animal. For each given group, the percentage protection is calculated as follows:

$P$=100−((average number of scratches of the group treated with the compound/average number of scratches of the group treated with the solvent)× 100)

This percentage protection is averaged for each group of animals (n=number of animals tested with the compound of the invention).

The protection percentages evaluated, in this model, for the most active compounds of the invention, used at the concentration of 500 μM, are between 20% and 100% (see example in table 4):

TABLE 4

| Compound no. | % P 500 μM |
|---|---|
| 2 | 72% |

The results of these assays show that the most active compounds of the invention block the effects induced by the stimulation of the TRPV1 receptors.

The compounds of the invention can therefore be used for the preparation of medicaments, in particular for the preparation of a medicament for preventing or treating pathologies in which TRPV1-type receptors are involved.

Thus, according to another of its aspects, a subject of the invention is medicaments which comprise a compound of formula (I), or a pharmaceutically acceptable salt, or else a hydrate or a solvate of said compound.

These medicaments can be used in therapeutics, in particular in the prevention and/or treatment of pain and inflammation, chronic pain, neuropathic pain (trauma-related, diabetic, metabolic, infection-related or toxic pain, or pain induced by an anticancer or iatrogenic treatment), (osteo-)arthritic pain, rheumatic pain, fibromyalgia, back pain, cancer-related pain, facial neuralgia, headaches, migraine, dental pain, burns, sunburn, animal bites or insect bites, post-herpetic neuralgia, muscle pain, trapped nerves (central and/or peripheral), spinal column and/or brain trauma, ischaemia (of the spinal column and/or of the brain), neurodegeneration, hemorrhagic strokes (of the spinal column and/or of the brain) and post-stroke pain.

The compounds of the invention can also be used for the preparation of a medicament for preventing and/or treating urological disorders such as bladder hyperactivity, bladder hyperreflexia, bladder instability, incontinence, urgent urination, urinary incontinence, cystitis, nephritic colic, pelvic hypersensitivity and pelvic pain.

The compounds of the invention can be used for the preparation of a medicament for preventing and/or treating gynecological disorders such as vulvodynia, pain associated with salpingitis or with dysmenorrhea.

These products can also be used for the preparation of a medicament for preventing and/or treating gastrointestinal disorders such as gastro-oesophageal reflex disorder, stomach ulcers, duodenal ulcers, functional dyspepsia, colitis, IBS, Crohn's disease, pancreatitis, oesophagitis or biliary colic.

The compounds of the invention can also be used for the preparation of a medicament for treating diabetes.

Similarly, the products of the present invention can be used in the prevention and/or treatment of respiratory disorders such as asthma, coughing, chronic obstructive pulmonary disease (COPD), bronchoconstriction and inflammatory disorders. These products can also be used for preventing and/or treating psoriasis, pruritis, dermal, ocular or mucosal irritations, herpes and shingles.

The compounds of the invention can also be used for the preparation of a medicament for treating depression.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are selected according to the pharmaceutical form and the method of administration desired, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its optional salt, solvate or hydrate, can be administered in unit administration form, as a mixture with conventional pharmaceutical excipients, to animals and to human beings for the prophylaxis or the treatment of the disorders or diseases mentioned above.

The appropriate unit administration forms include oral forms such as tablets, soft or hard gelatine capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

Said unit forms are dosed so as to allow a daily administration of from 0.001 to 30 mg of active ingredient per kg of body weight, according to the galenic form.

There may be specific cases where higher or lower dosages are appropriate: such dosages do not depart from the scope of the invention. According to the usual practice, the dosage appropriate for each patient is determined by the physician according to the method of administration and the weight and response of said patient.

According to another of its aspects, the present invention also relates to a method for treating the pathologies indicated above, which comprises the administration, to a patient, of an effective dose of at least one compound according to the invention, or a pharmaceutically acceptable salt, a hydrate or a solvate thereof.

What is claimed is:

1. A compound of formula (I):

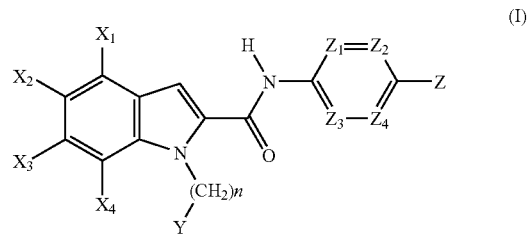

in which $X_1$ is hydrogen, halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, cyano, C(O)NR$_1$R$_2$, nitro, $C_1$-$C_6$-thioalkyl, —S(O)—$C_1$-$C_6$-alkyl, —S(O)$_2$—$C_1$-$C_6$-alkyl, SO$_2$NR$_1$R$_2$, aryl-$C_1$-$C_6$-alkylene, aryl or heteroaryl group, the aryl and heteroaryl being optionally substituted with one or more substituents selected from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$X_2$ is hydrogen, halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxyl, cyano, C(O)NR$_1$R$_2$, $C_1$-$C_6$-thioalkyl, —S(O)—$C_1$-$C_6$-alkyl, —S(O)$_2$ —$C_1$-$C_6$-alkyl, SO$_2$NR$_1$R$_2$, aryl-$C_1$-$C_6$-alkylene, aryl or heteroaryl group, the aryl and the heteroaryl being optionally substituted with one or more substituents selected from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$X_3$ and $X_4$, independently of one another, are hydrogen, halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$, aryl-$C_1$-$C_6$-alkylene, aryl or heteroaryl group, the aryl and the heteroaryl being optionally substituted with one or more substituents selected from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$Z_1$, $Z_2$, $Z_3$ and $Z_4$, independently of one another, are nitrogen or C(R$_6$) group, wherein at least one of which is nitrogen and at least one of which is C(R$_6$) group; the nitrogen atom or one of the nitrogen atoms present in the ring, defined as nitrogen in the 1-position, being optionally substituted with R$_7$ when the carbon atom in the 2- or 4-position with respect to this reference nitrogen is substituted with an oxo or thio group;

n is equal to 0, 1, 2 or 3;

Y is aryl or heteroaryl optionally substituted with one or more groups selected from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxy, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxyl, cyano, C(O)NR$_1$R$_2$, nitro, NR$_1$R$_2$, $C_1$-$C_6$-thioalkyl, thiol, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$, aryl-$C_1$-$C_6$-alkylene or aryl group, the aryl and the aryl-$C_1$-$C_6$-alkylene being optionally substituted with one or more substituents selected from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

Z is a cyclic amine attached via the nitrogen atom, of formula:

in which

A is $C_1$-$C_7$-alkylene optionally substituted with one or two groups R$_8$;

B is $C_1$-$C_7$-alkylene group optionally substituted with one or two groups R$_9$;

L is a bond, sulfur, oxygen, NR$_{10}$ or NR$_{11}$, the carbon atoms of the cyclic amine Z being optionally substituted with one or more groups R$_{12}$ which may be identical to or different from one another;

R$_1$ and R$_2$, independently of one another, are hydrogen, $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group; or R$_1$ and R$_2$ taken together with the nitrogen atom to which they are attached form azetidinyl, pyrrolidinyl, piperidinyl, azepinyl, morpholinyl, thiomorpholinyl, piperazinyl or homopiperazinyl group, this group being optionally substituted with $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

R$_3$ and R$_4$, independently of one another, are hydrogen, $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

R$_5$ is a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

R$_6$ is hydrogen, halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, $C_1$-$C_6$-thioalkyl, —S(O)—$C_1$-$C_6$-alkyl, —S(O)$_2$—$C_1$-$C_6$-alkyl, aryl, aryl-$C_1$-$C_6$-alkylene, heteroaryl, hydroxy, thiol, oxo or thio group;

R$_7$ is hydrogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, aryl, aryl-$C_1$-$C_6$-alkylene or heteroaryl group;

R$_8$, R$_9$ and R$_{10}$ are defined such that:

two groups R$_8$ can together form a bond or a $C_1$-$C_6$-alkylene group;

two groups R$_9$ can together form a bond or a $C_1$-$C_6$-alkylene group;

R$_8$ and R$_9$ can together form a bond or a $C_1$-$C_6$-alkylene group;

R$_8$ and R$_{10}$ can together form a bond or a $C_1$-$C_6$-alkylene group;

R$_9$ and R$_{10}$ can together form a bond or a $C_1$-$C_6$-alkylene group;

R$_{11}$ is hydrogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, hydroxy, COOR$_5$, C(O)NR$_1$R$_2$, aryl-$C_1$-$C_6$-alkylene, aryl or heteroaryl group, the aryl and the heteroaryl being optionally substituted with one or more substituents selected from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_1$-$C_6$-fluoroalkoxy, nitro or cyano group;

R$_{12}$ is fluorine, $C_1$-$C_6$-alkyl optionally substituted with R$_{13}$, $C_3$-$C_7$-cycloalkyl, $C_3$-$C_7$-cycloalkyl-$C_1$-$C_3$-alkylene, $C_1$-$C_6$-fluoroalkyl or $C_1$-$C_6$-cycloalkyl-1,1-idinyl group, a $C_3$-$C_7$-heterocycloalkyl-1,1-idinyl group optionally substituted on a nitrogen atom with a group R$_{11}$, or a $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, C(O)NR$_1$R$_2$, NR$_1$R$_2$, NR$_3$COR$_4$, OC(O)NR$_1$R$_2$, NR$_3$COOR$_5$, NR$_3$CONR$_1$R$_2$, hydroxy, thiol, oxo, thio, aryl-$C_1$-$C_6$-alkylene or aryl group, the aryl being optionally substituted with one or more substituents selected from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_1$-$C_6$-fluoroalkoxy, nitro or cyano group;

39

$R_{13}$ is a $C_1$-$C_6$-alkoxy, $C_3$-$C_7$-cycloalkoxy, $C_3$-$C_7$-cycloalkyl-$C_1$-$C_6$-alkylene-O—, $C(O)NR_1R_2$, $NR_1R_2$, $NR_3COR_4$, $OC(O)NR_1R_2$, $NR_3COOR_5$ or hydroxy; and it being possible for the nitrogen atom(s) of the compound of formula (I) to be in oxidized form; and it being possible for the sulfur atom(s) of the compound of formula (I) to be in oxidized form;

or an addition salt thereof.

2. The compound of formula (I) according to claim 1, wherein $X_1$, $X_2$, $X_3$ and $X_4$ are selected, independently of one another, from hydrogen, halogen, $C_1$-$C_6$-alkyl, $C_1$-$C_6$-fluoroalkyl, $C_1$-$C_6$-thioalkyl or —$S(O)_2$—$C_1$-$C_6$-alkyl;

or an addition salt thereof.

3. The compound of formula (I) according to claim 1, wherein $X_1$ is hydrogen, halogen or $C_1$-$C_6$-alkyl;

$X_2$ is hydrogen, halogen, $C_1$-$C_6$-alkyl, $C_1$-$C_6$-fluoroalkyl or —$S(O)_2$—$C_1$-$C_6$-alkyl;

$X_3$ and $X_4$, independently of one another, are hydrogen, halogen, $C_1$-$C_6$-alkyl, $C_1$-$C_6$-fluoroalkyl, $C_1$-$C_6$-alkoxy, $NR_1R_2$ or $C_1$-$C_6$-thioalkyl; and $R_1$ and $R_2$, independently of one another, are $C_1$-$C_6$-alkyl;

or an addition salt thereof.

4. The compound of formula (I) according to claim 1, wherein $Z_1$, $Z_2$, $Z_3$ and $Z_4$ are, independently of one another, nitrogen or $C(R_6)$ group of which at least two of them are $C(R_6)$ group; the nitrogen atom or one of the nitrogen atoms present in the ring, defined as nitrogen in the 1-position, being optionally substituted with $R_7$ when the carbon atom in the 2- or 4-position with respect to this reference nitrogen is substituted with an oxo or thio group; and $R_6$ and $R_7$ being as defined in claim 1;

or an addition salt thereof.

5. The compound of formula (I) according to claim 4, wherein $Z_1$ and $Z_3$ are $C(R_6)$ group and $Z_2$ and $Z_4$ are nitrogen; and wherein $R_6$ is hydrogen;

or an addition salt thereof.

6. The compound of formula (I) according to claim 4, wherein $Z_1$, $Z_2$, $Z_3$ and $Z_4$ are, independently of one another, nitrogen or $C(R_6)$ group, one of which is nitrogen and the others are $C(R_6)$ group; the nitrogen atom present in the cycle, defined as nitrogen in the 1-position, being optionally substituted with $R_7$ when the carbon atom in the 2- or 4-position with respect to this reference nitrogen is substituted with an oxo or thio group; and $R_6$ and $R_7$ being as defined in claim 1;

or an addition salt thereof.

7. The compound of formula (I) according to claim 6, wherein:

$Z_4$ is nitrogen and $Z_1$, $Z_2$ and $Z_3$ are, independently of one another, $C(R_6)$ group;

and wherein $R_6$ is hydrogen or $C_1$-$C_6$-alkyl, $C_1$-$C_6$-fluoroalkyl or $C_1$-$C_6$-alkoxyl;

or an addition salt thereof.

8. The compound of formula (I) according to claim 1, wherein n is equal to 1;

or an addition salt thereof.

9. The compound of formula (I) according to claim 1, wherein Y is an aryl or a heteroaryl optionally substituted with one or more groups selected from halogen, $C_1$-$C_6$-alkyl or $NR_1R_2$; and wherein $R_1$ and $R_2$ taken together with the nitrogen atom to which they are attached form azetidinyl, pyrrolidinyl, piperidinyl, azepinyl, morpholinyl, thiomorpholinyl, piperazinyl or homopiperazinyl group, this group being optionally substituted with $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

40 or an addition salt thereof.

10. The compound of formula (I) according to claim 1, wherein:

Z is a cyclic amine attached via the nitrogen atom, of formula:

in which

A is $C_1$-$C_4$-alkylene group optionally substituted with one or two groups $R_8$;

B is $C_1$-$C_4$-alkylene group optionally substituted with one or two groups $R_9$;

L is a bond or oxygen;

it being possible for the nitrogen of the cyclic amine Z to be in N-oxide form;

the carbon atoms of the cyclic amine Z being optionally substituted with a group $R_{12}$;

$R_8$ and $R_9$ are defined such that:

two groups $R_8$ can together form a bond; or two groups $R_9$ can together form a bond; or $R_8$ and $R_9$ can together form a bond;

$R_{12}$ is $NR_1R_2$, $NR_3COOR_5$ or hydroxy;

$R_1$ and $R_2$ are, independently of one another, hydrogen;

$R_3$ is hydrogen; and $R_5$ is $C_1$-$C_6$-alkyl;

or an addition salt thereof.

11. The compound of formula (I) according to claim 10, wherein:

Z is a cyclic amine selected from azetidine, pyrrolidine, piperidine, morpholine, azabicylo[3.1.0]hexane and azabicylo[3.2.0]heptane;

it being possible for the nitrogen atom of the cyclic amine Z to be in N-oxide form;

the carbon atoms of the cyclic amine Z being optionally substituted with a group $R_{12}$;

$R_{12}$ is $NR_1R_2$, $NR_3COOR_5$ or hydroxy;

$R_1$ and $R_2$ are, independently of one another, hydrogen;

$R_3$ is hydrogen; and $R_5$ is $C_1$-$C_6$-alkyl;

or an addition salt thereof.

12. The compound of formula (I) according to claim 11, wherein:

Z is a cyclic amine selected from azetidine, pyrrolidine, piperidine, morpholine, azabicylo[3.1.0]hexane and azabicylo[3.2.0]heptane;

the carbon atoms of the azetidine being optionally substituted with hydroxy;

the carbon atoms of the pyrrolidine being optionally substituted with $NR_1R_2$, $NR_3COOR_5$ or hydroxy; it being possible for the nitrogen atom of the pyrrolidine to be in N-oxide form;

$R_1$ and $R_2$ are, independently of one another, hydrogen;

$R_3$ is hydrogen; and $R_5$ is $C_1$-$C_6$-alkyl;

or an addition salt thereof.

13. A process for preparing a compound of formula (I) according to claim 1 comprising:
reacting a compound of formula (IV):

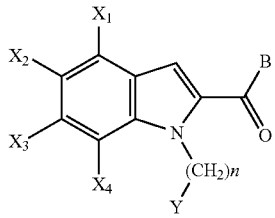

in which $X_1$, $X_2$, $X_3$, $X_4$, Y and n are as defined in claim 1 and B is chlorine, with an amine of formula (V):

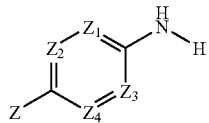

in which $Z_1$, $Z_2$, $Z_3$, $Z_4$ and Z are as defined in claim 1, in a solvent.

14. A process for preparing a compound of formula (I) according to claim 1 comprising:
reacting a compound of formula (IV):

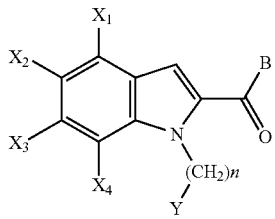

in which $X_1$, $X_2$, $X_3$, $X_4$, Y and n are as defined in claim 1 and B is hydroxy, with an amine of formula (V):

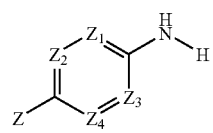

in which $Z_1$, $Z_2$, $Z_3$, $Z_4$ and Z are as defined in claim 1, in the presence of a coupling agent and a base in a solvent.

15. A process for preparing a compound of formula (I) according to claim 1 comprising:
reacting a compound of formula (VI):

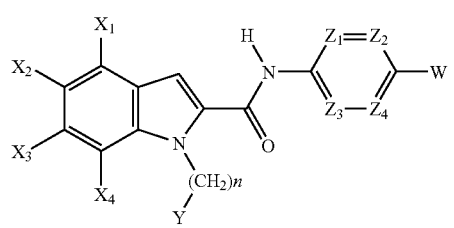

in which $X_1$, $X_2$, $X_3$, $X_4$, $Z_1$, $Z_2$, $Z_3$, $Z_4$, Y and n are as defined in claim 1 and W is halogen,
with an amine of formula ZH in which Z is a cyclic amine as defined in claim 1.

16. A pharmaceutical composition comprising a compound of formula (I) according to claim 1 or a pharmaceutically acceptable salt thereof in combination with at least one pharmaceutically acceptable excipient.

17. A pharmaceutical composition comprising a compound of formula (I) according to claim 12 or a pharmaceutically acceptable salt thereof in combination with at least one pharmaceutically acceptable excipient.

* * * * *

UNITED STATES PATENT AND TRADEMARK OFFICE
CERTIFICATE OF CORRECTION

PATENT NO. : 7,786,104 B2
APPLICATION NO. : 12/359468
DATED : August 31, 2010
INVENTOR(S) : Laurent DuBois et al.

It is certified that error appears in the above-identified patent and that said Letters Patent is hereby corrected as shown below:

In column 3, line 61, delete "azabicylo" and insert -- azabicyclo --, therefor.
In column 3, line 61, delete "azabicylo" and insert -- azabicyclo --, therefor.
In column 3, line 62, delete "azabicylo" and insert -- azabicyclo --, therefor.
In column 3, line 62, delete "diazabicylo" and insert -- diazabicyclo --, therefor.
In column 3, line 63, delete "azabicylo" and insert -- azabicyclo --, therefor.
In column 3, line 63, delete "diazabicylo" and insert -- diazabicyclo --, therefor.
In column 3, line 64, delete "azabicylo" and insert -- azabicyclo --, therefor.
In column 6, line 19, delete "azabicylo" and insert -- azabicyclo --, therefor.
In column 6, line 19, delete "azabicylo" and insert -- azabicyclo --, therefor.
In column 6, line 38, delete "azabicylo" and insert -- azabicyclo --, therefor.
In column 6, line 38, delete "azabicylo" and insert -- azabicyclo --, therefor.
In column 6, line 56, delete "azabicylo" and insert -- azabicyclo --, therefor.
In column 6, line 56, delete "azabicylo" and insert -- azabicyclo --, therefor.
In column 7, line 9, delete "azabicylo" and insert -- azabicyclo --, therefor.
In column 7, line 9, delete "azabicylo" and insert -- azabicyclo --, therefor.
In column 25, line 25, delete "Amine" and insert -- amine --, therefor.
In column 27, line 24, delete "Acid" and insert -- acid --, therefor.
In column 40, line 40, in claim 11, delete "azabicylo" and insert -- azabicyclo --, therefor.
In column 40, line 41, in claim 11, delete "azabicylo" and insert -- azabicyclo --, therefor.
In column 40, line 55, in claim 12, delete "azabicylo" and insert -- azabicyclo --, therefor.
In column 40, line 56, in claim 12, delete "azabicylo" and insert -- azabicyclo --, therefor.

Signed and Sealed this
Twenty-sixth Day of July, 2011

David J. Kappos
*Director of the United States Patent and Trademark Office*